(12) United States Patent
Palmeri et al.

(10) Patent No.: US 8,398,549 B2
(45) Date of Patent: Mar. 19, 2013

(54) ULTRASOUND METHODS, SYSTEMS AND COMPUTER PROGRAM PRODUCTS FOR IMAGING CONTRASTING OBJECTS USING COMBINED IMAGES

(75) Inventors: Mark L. Palmeri, Durham, NC (US); Veronica Rotemberg, Durham, NC (US); Stephen J. Rosenzweig, Durham, NC (US); Kathryn R. Nightingale, Durham, NC (US)

(73) Assignee: Duke University, Durham, NC (US)

( * ) Notice: Subject to any disclaimer, the term of this patent is extended or adjusted under 35 U.S.C. 154(b) by 623 days.

(21) Appl. No.: 12/706,269

(22) Filed: Feb. 16, 2010

(65) Prior Publication Data

US 2011/0201931 A1    Aug. 18, 2011

(51) Int. Cl.
*A61B 8/00*    (2006.01)
(52) U.S. Cl. .................. 600/437; 600/440; 600/458
(58) Field of Classification Search .................. 600/437, 600/440, 458
See application file for complete search history.

(56) References Cited

U.S. PATENT DOCUMENTS

| | | | |
|---|---|---|---|
| 6,371,912 B1 * | 4/2002 | Nightingale et al. | 600/437 |
| 6,951,544 B2 * | 10/2005 | Trahey et al. | 600/449 |
| 2005/0215899 A1 * | 9/2005 | Trahey et al. | 600/439 |
| 2010/0069751 A1 * | 3/2010 | Hazard et al. | 600/438 |

OTHER PUBLICATIONS

Chin et al; Needle Visualization in Ultrasound-Guided Regional Anesthesia: Challenges and Solutions; Regional Anesthesia and Pain Medicine, vol. 33, No. 6 (Nov.-Dec. 2008): pp. 532-544.

Gray, Andrew T.; "Ultrasound-guided Regional Anesthesia"; Anesthesiology, vol. 104, No. 2, Feb. 2006 pp. 368-373.

Palmeri et al; "Ultrasonic Tracking of Acoustic Radiation Force-Induced Displacements in Homogeneous Media"; IEEE Transactions on Ultrasonics, Ferroelectrics, and Frequency Control, vol. 53, No. 7, Jul. 2006, pp. 1300-1313.

Palmeri et al; "A Finite-Element Method Model of Soft Tissue Response to Impulsive Acoustic Radiation Force"; NIH-PA Author Manuscript; IEEE Trans Ultrason Ferroelectr Freq Control. Oct. 2006; 52 (10) pp. 1-34.

Palmeri et al; On the Feasibility of Imaging Peripheral Nerves Using Acoustic Radiation Force Impulse Imaging; NIH-PA Author Manuscript; Ultrason Imaging. Jul. 2009; 31 (3) pp. 172-182.

Wang, Xin; Laplacian Operator-Based Edge Detectors; IEEE Transactions on Pattern Analysis and Machine Intelligence, vol. 29, No. 5, May 2007; pp. 886-890.

Palmeri, et al; Improved Needle Visualization Using Acoustic Radiation Force-Based Image Mapping Algorithms, ASA Abstracts, http://www.asaabstracts.com/strands/asaabstracts/pringAbstract.htm;jsessionid=8D. Oct. 18, 2009.

* cited by examiner

*Primary Examiner* — Peter Luong
(74) *Attorney, Agent, or Firm* — Myers Bigel Sibley & Sajovec

(57) ABSTRACT

A system for identifying a presence of an object in a tissue region of interest includes a controller configured to obtain first and second image data sets from the region of interest. A contrast identification module is configured to identify a contrasting region of altered stiffness in the first image data set corresponding to an object in the tissue region of interest. An image data enhancement module is configured to identify the object in the second image data set based on the contrasting region of altered stiffness in the first image data set.

20 Claims, 21 Drawing Sheets

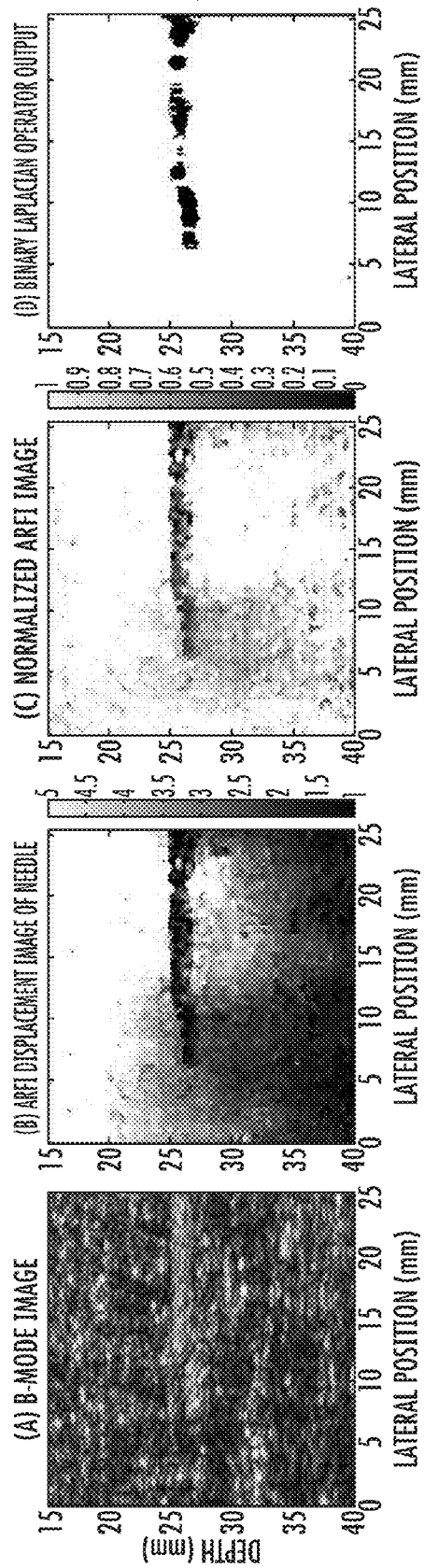

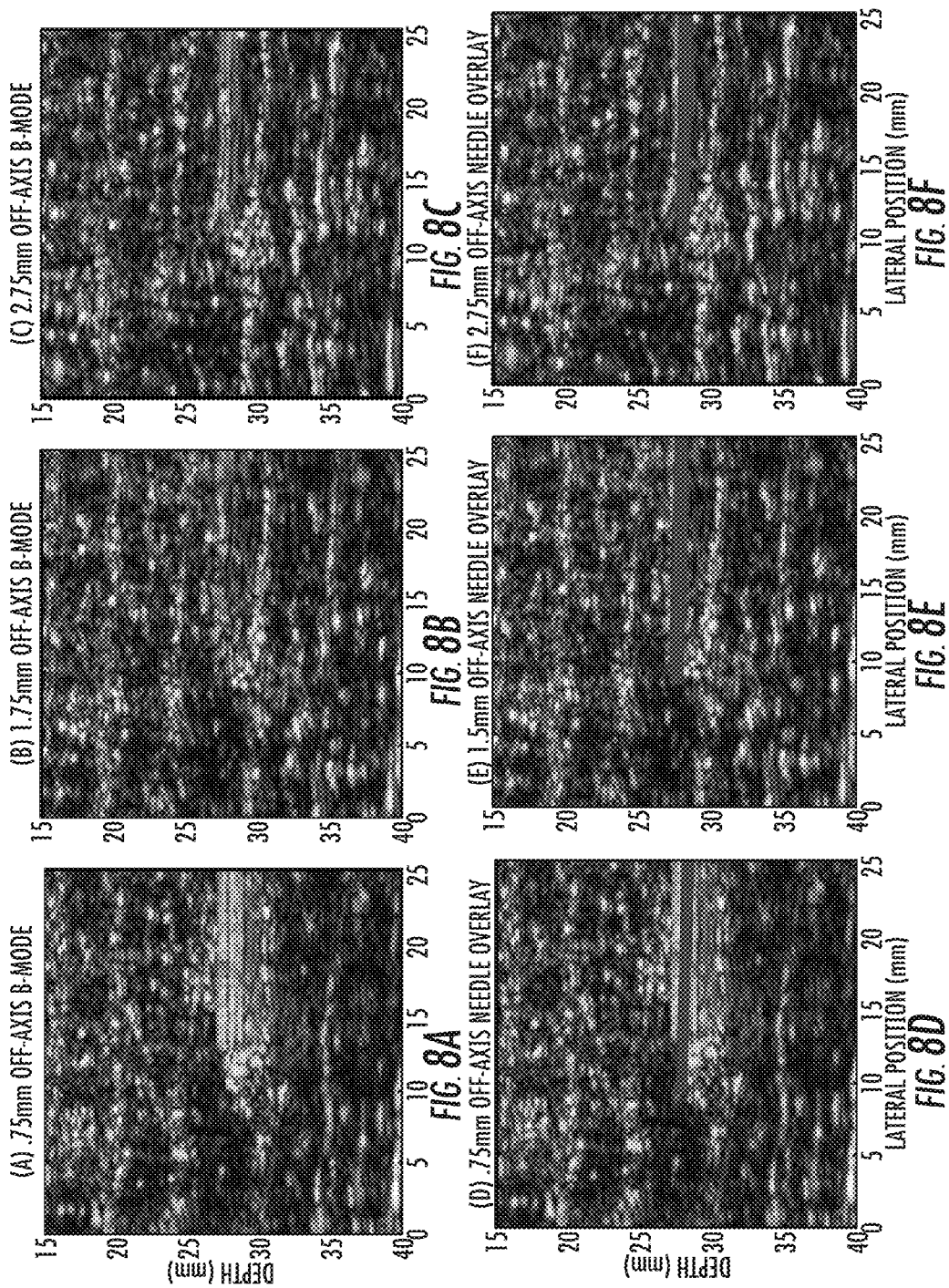

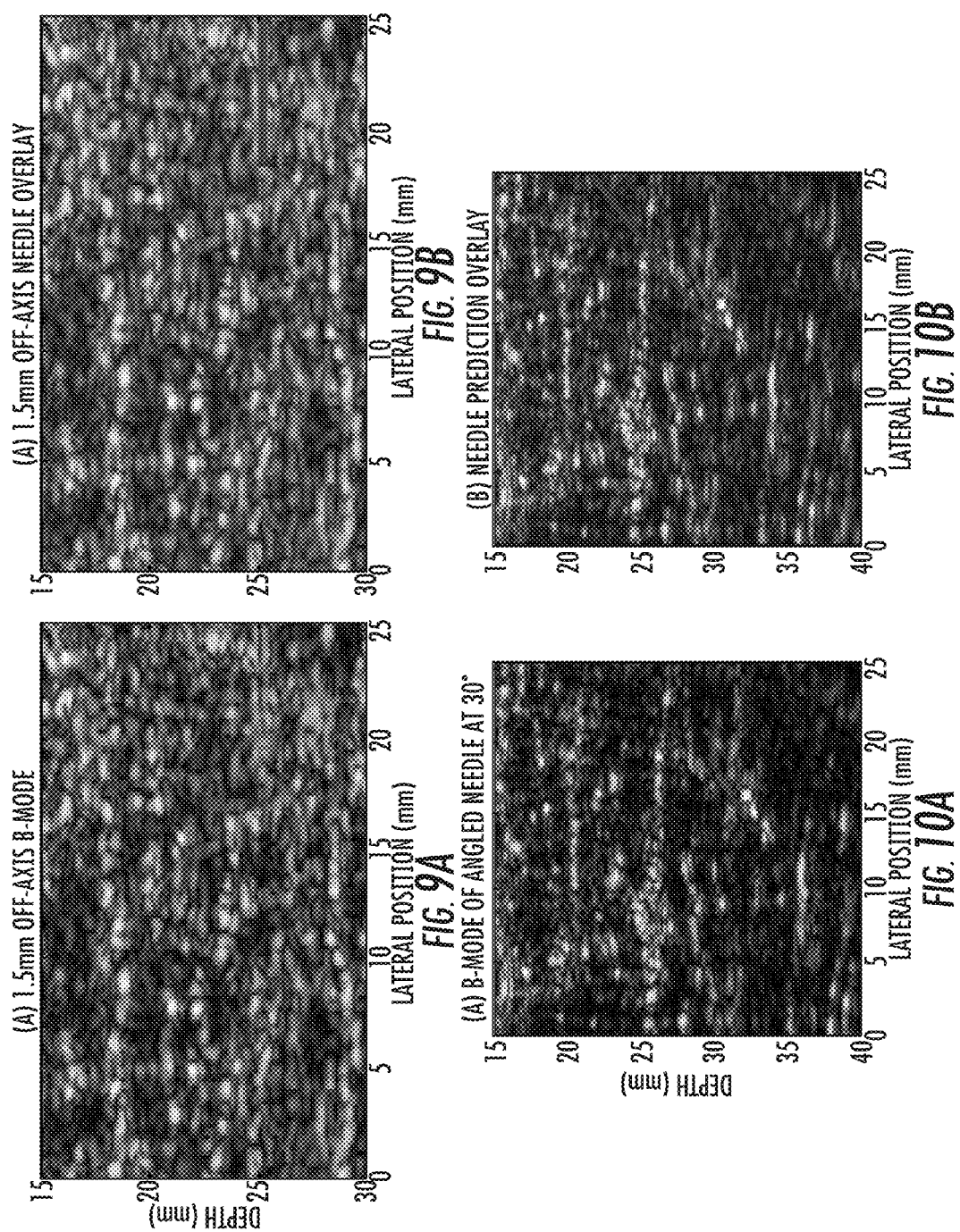

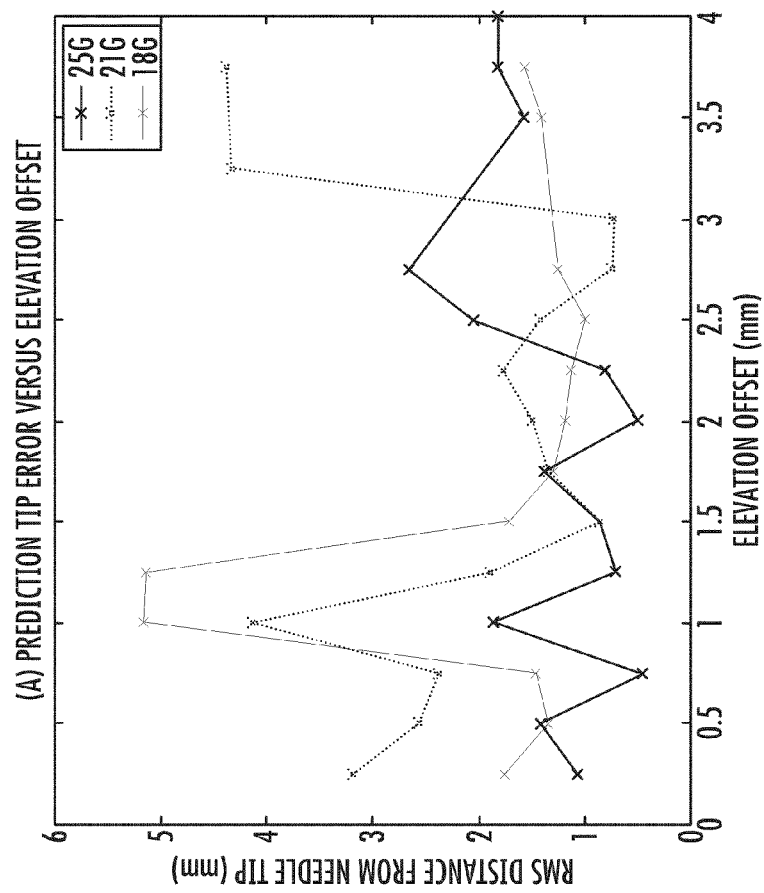
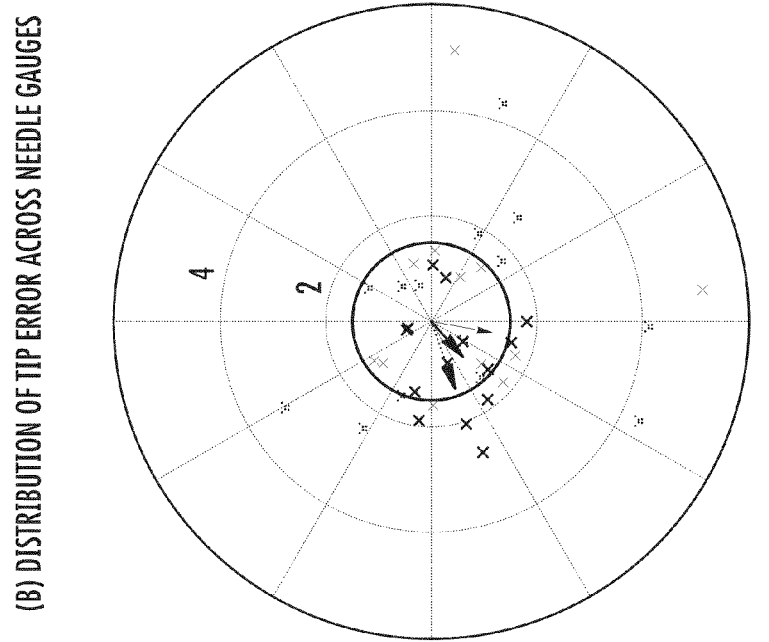
FIG. 12A
FIG. 12B

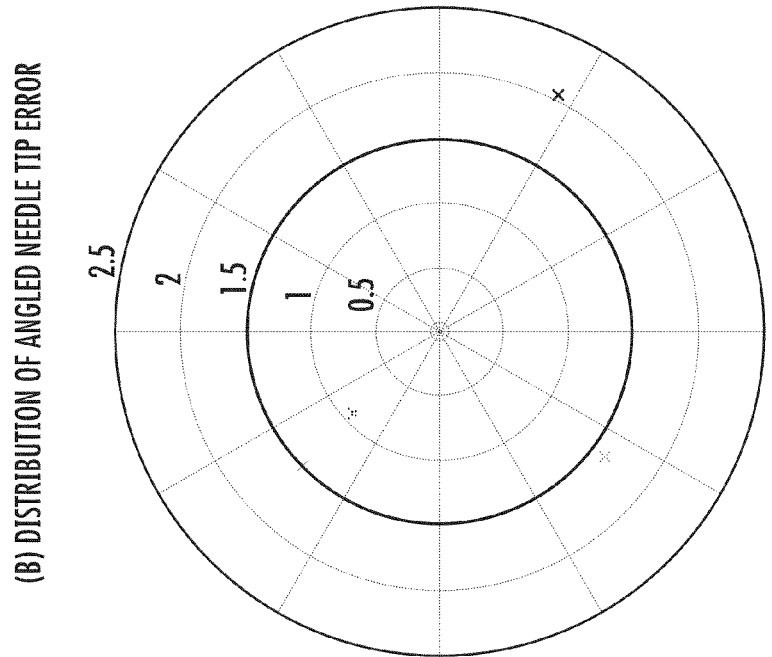
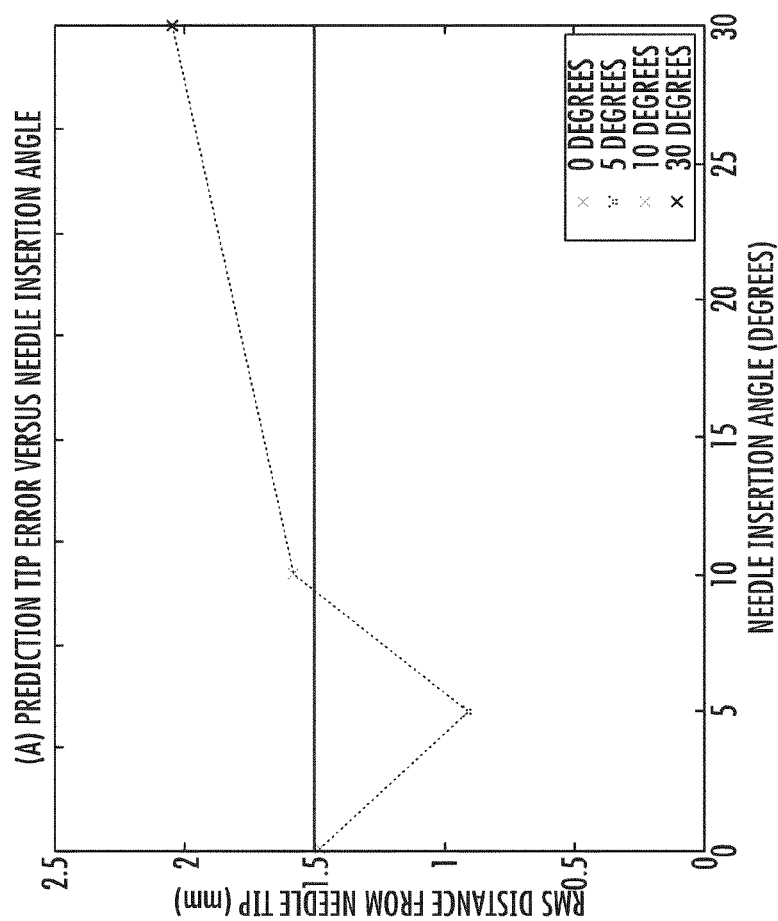
FIG. 13B
FIG. 13A

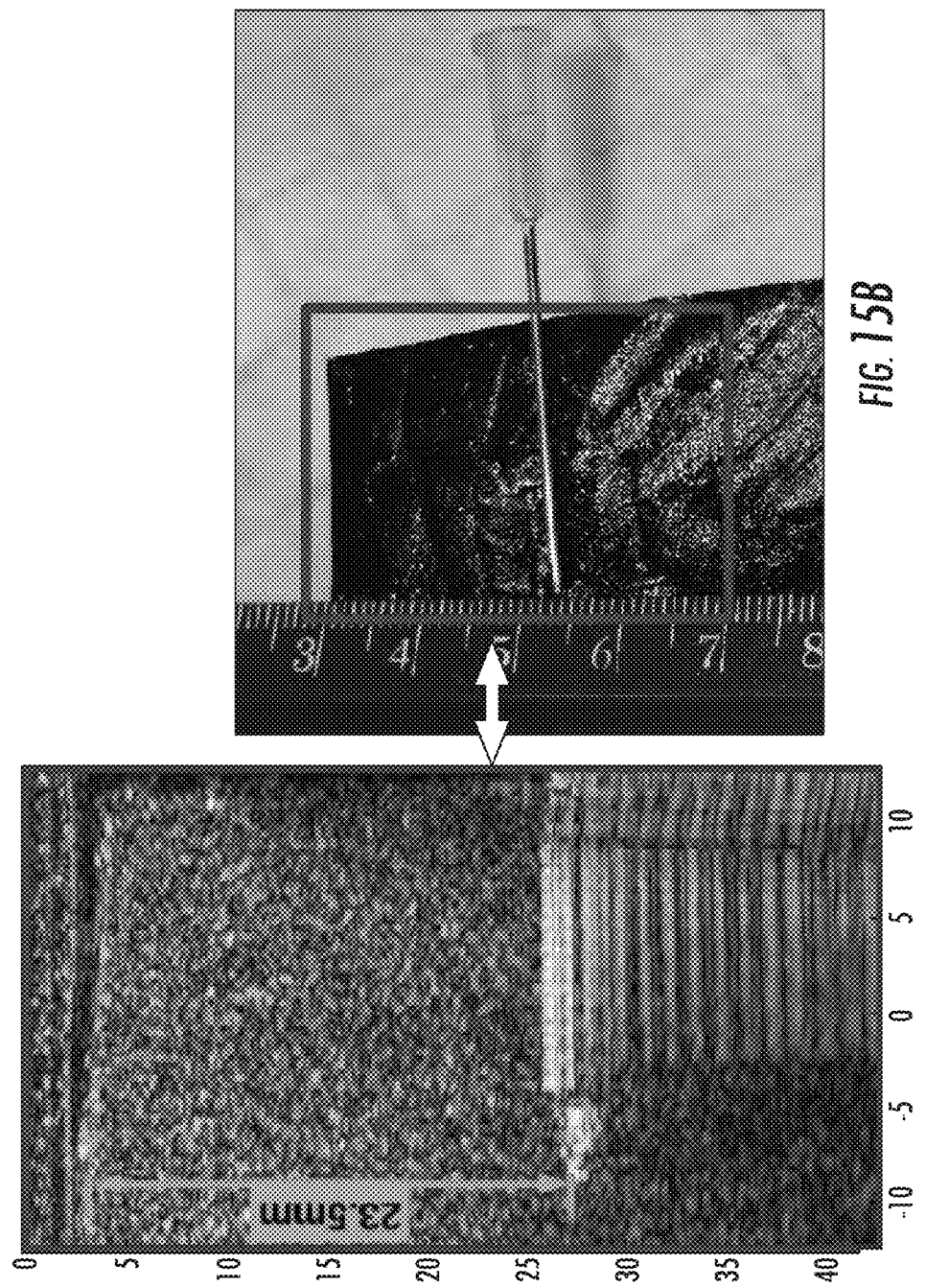

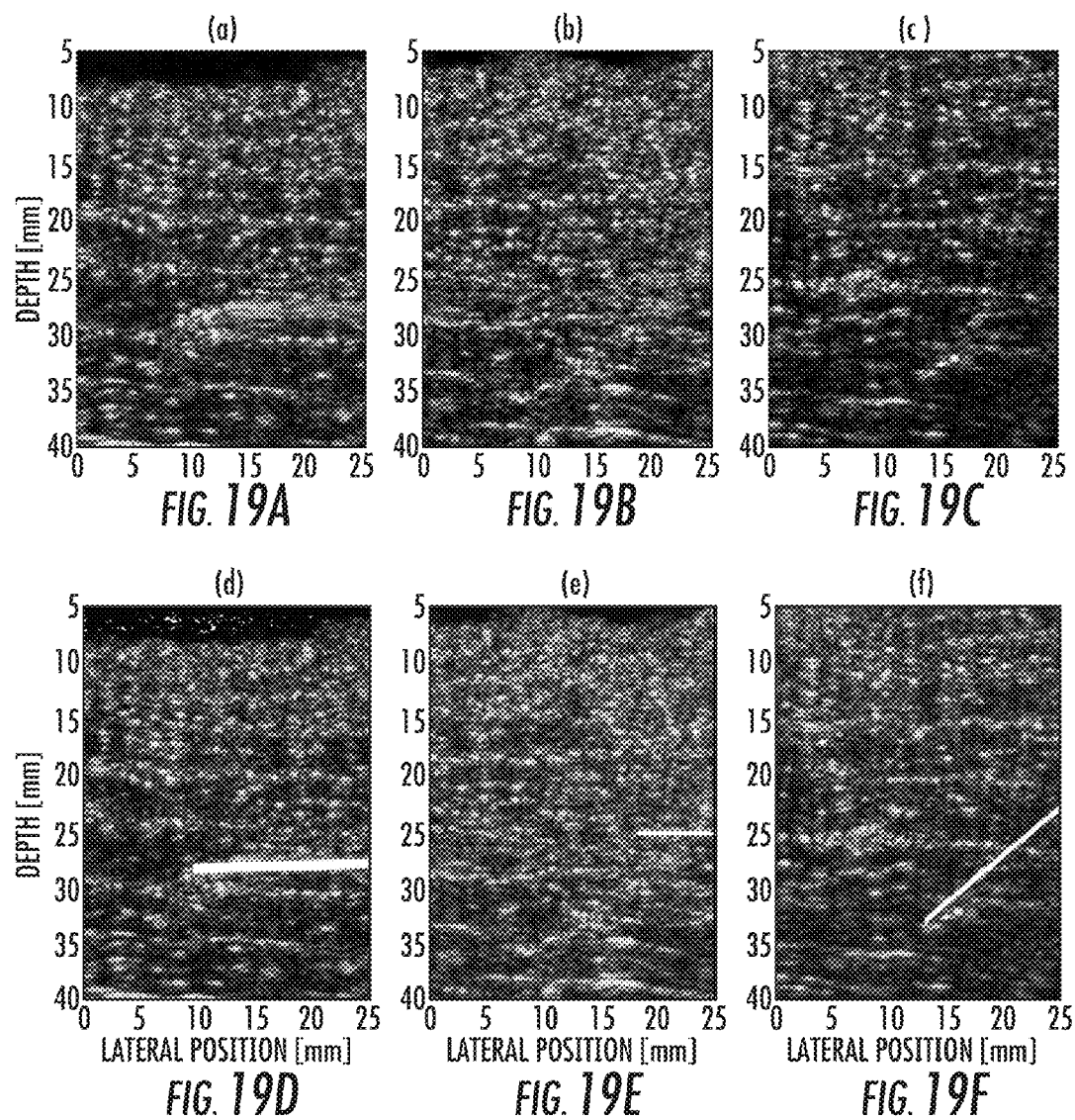

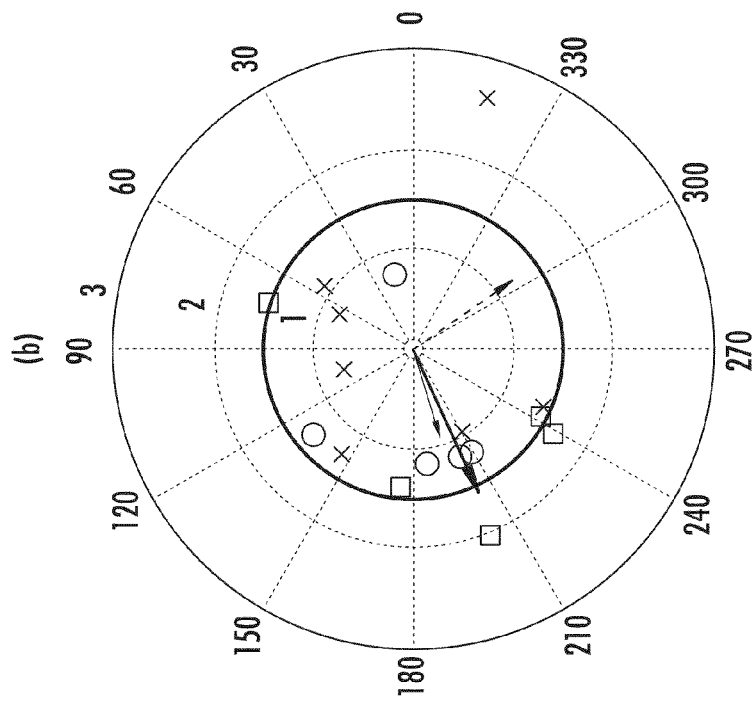
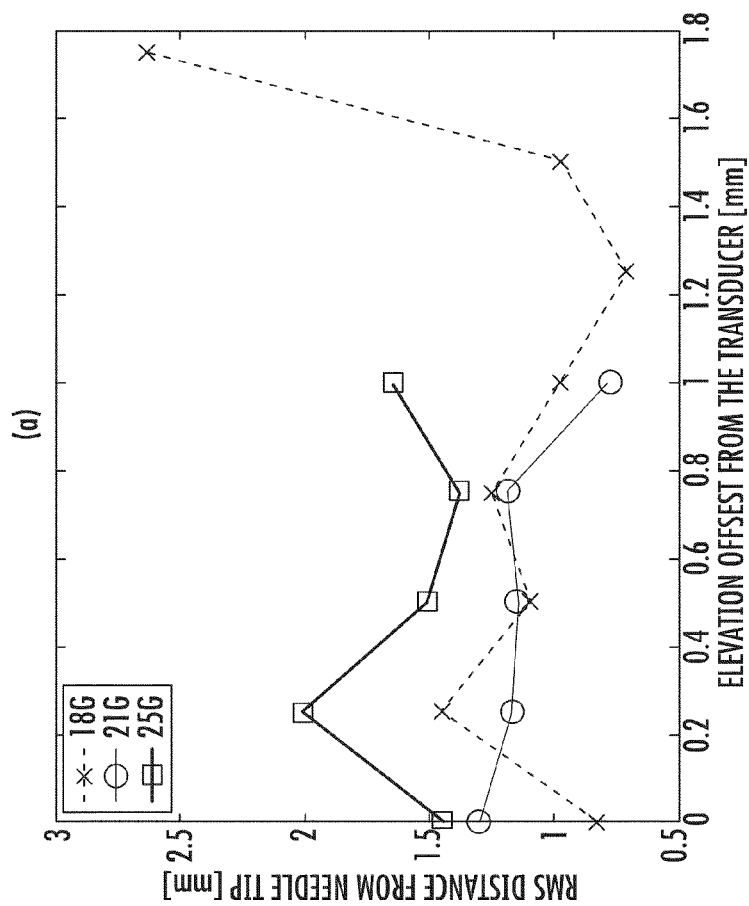
FIG. 21B
FIG. 21A

ULTRASOUND METHODS, SYSTEMS AND COMPUTER PROGRAM PRODUCTS FOR IMAGING CONTRASTING OBJECTS USING COMBINED IMAGES

GOVERNMENT SUPPORT

This invention was made with Government support under grant number grant numbers R01-CA114075 and R01-EB002312 from the National Institute of Health. The Government has certain rights to this invention.

FIELD OF THE INVENTION

The present invention relates to ultrasound methods, systems and computer program products, and more specifically to ultrasound imaging of contrasting objects in tissue.

BACKGROUND

Ultrasound-assisted guidance is used for permanent or temporary placement of various medical devices, including catheters, needles, endoscopes and the like. For example, ultrasound-guided needle placement is widely used in the clinical setting, particularly for central venous catheter placement, tissue biopsy guidance and regional anesthesia. In these two areas, B-mode ultrasound has been useful to aid needle guidance, increase success rate, and prevent injuries to surrounding tissues. J. French, N. Raine-Fenning, N. Hardman, and N. Bedforth, "Pitfalls of ultrasound guided vascular access: the use of three/four-dimensional ultrasound," *Anaesthesia*, vol. 63, pp. 806-813, 2008; M. Abrahams, M. Aziz, R. Fu, and J.-L. Horn, "Ultrasound guidance compared with electrical neurostimulation for peripheral nerve block: a systematic review and meta-analysis of randomized controlled trials," *British Journal of Anaesthesia*, vol. 103, no. 3, pp. 408-417, 2009. However, conventional B-mode images may be susceptible to various difficulties in needle visualization. For example, difficulties in needle visualization and, consequently, accurate needle placement may occur if the needle is not in an exactly specified orientation to the transducer, the nerve or the central vein. Difficulties with ultrasound guidance in these areas often result from steep needle insertion angle and spatial offset between the imaging plane and the needle.

Various attempts to improve image visualization in ultrasound image data have been attempted. For example, medical devices can include a coating or dimpling pattern to increase visualization. Attempts have also been made to vibrate an inserted needle for Doppler imaging.

SUMMARY OF EMBODIMENTS OF THE INVENTION

According to some embodiments of the invention, a system for identifying a presence of an object in a tissue region of interest includes a controller configured to obtain first and second image data sets from the region of interest. A contrast identification module is configured to identify a contrasting region of altered stiffness in the first image data set corresponding to an object in the tissue region of interest. An image data enhancement module is configured to identify the object in the second image data set based on the contrasting region of altered stiffness in the first image data set.

In some embodiments, the first image data set is an Acoustic Radiation Force Impulse (ARFI) image data set that is obtained concurrently with the second image data set. The second image data set may be a B-mode image data set. The image data enhancement module may be further configured to enhance a contrast level of the region of altered stiffness corresponding to the object. In some embodiments, the image data enhancement module is configured to determine a third image data set that comprises at least a portion of the first image data set and at least a portion of the second image data set. The third image data set may include the B-mode image data set and the region of altered stiffness from the ARFI image data set.

In some embodiments, the object includes a medical device. The image data enhancement module may be configured to identify the object based on predetermined characteristics of the object. In some embodiments, the object includes an elongated needle, and the image enhancement module is configured to conform the region of increased stiffness to generally correspond to an elongated shape corresponding to the needle. In some embodiments, the image enhancement module is configured to identify a location of a tip portion of the needle.

In some embodiments according to the invention, methods for identifying a presence of an object in a tissue region of interest using imaging include obtaining first and second image data sets from the region of interest. A contrasting region of altered stiffness in the first image data set corresponding to an object in the tissue region of interest is identified. The object is identified in the second image data set based on the contrasting region of altered stiffness in the first image data set.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4A is B-mode image data of the lateral position of an 18 G longitudinally acquired needle in lean bovine muscle 2 mm offset in elevation from the imaging plane as a function of depth according to some embodiments of the invention.

FIG. 4B is an initial Acoustic Radiation Force Impulse (ARFI) image of the needle in FIG. 4A.

FIG. 4C is a normalized ARFI image of the image data of FIG. 4B prior to median filtration.

FIG. 4D is the output of a Laplacian operator with contrast thresholds of the image data of FIGS. 4A-4C according to some embodiments of the invention.

FIGS. 8A-8F are B-mode images of a horizontal 21 G needle in a lean bovine muscle at several locations operationally off-axis from the transducer without enhanced needle visualization based on an ARFI image (FIGS. 8A-8C) and with enhanced needle visualization based on a corresponding ARFI image (FIGS. 8D-8F). The needle in FIG. 8A and FIG. 8D has a 0.75 mm elevation offset from the transducer. The needle in FIG. 8B and FIG. 8E has a 1.5 mm elevation offset from the transducer. The needle in FIG. 8C and FIG. 8F has a 2.75 mm elevation offset from the transducer.

FIG. 9A is a B-mode image of a horizontal 25 G needle in lean bovine muscle with a 1.5 mm elevation offset from the transducer.

FIG. 9B is the B-mode image of FIG. 9A with a region of increased stiffness from a corresponding ARFI image overlay to enhance the needle location.

FIG. 10A is a B-mode image of an 18 G needle at 30 degrees from the horizontal with respect to the transducer in lean bovine muscle.

FIG. 10B is the B-mode image of FIG. 10A with a region of increased stiffness from a corresponding ARFI image overlay to enhance the needle location.

FIG. 12A is a graph of the root mean square (RMS) error of needle tip prediction as a function of elevation offset from the transducer. As the transducer movers farther away from the axis of the needle, the tip prediction becomes more accurate for the 18 G and 21 G needles, but as the transducer moves more than 2.5 mm from the axis of the needle, the 21 G and 25 G predictions become less accurate.

FIG. 12B is a graph of the distribution of actual needle tip location versus needle tip prediction across all elevation offset distances in the lateral/axial plane for the three needle gauges. The inner circle represents a 1.5 mm radius around the actual needle tip position and the arrows represent the mean tip prediction error for each needle gauge.

FIG. 13A is a graph of the needle insertion angle as a function of distance from the needle tip. FIG. 13B is a graph of the distribution of angled needle tip error. FIGS. 13A-13B illustrate the needle tip prediction error as compared to manual tip identification using decorrelation maps for angled needles.

FIGS. 15A-B are digital images of a needle in a 200 bloom graphite phantom. FIG. 15B is a demonstration of axial tip location measurement in the 200 bloom graphite phantom. After measuring the needle location, the location was determined in the B-mode images using the distances from the edge of the phantom as shown in FIG. 15A. The needle tip was identified by measuring the lateral and axial distances of the tip from the edges of the phantom in the needle plane.

FIGS. 16A and 16D show no elevation offset from the transducer, FIGS. 16B and 16E show a 0.5 mm elevation offset, and FIGS. 16C and 16F show a 1 mm elevation offset. The "X" in each image of FIGS. 16D-16F indicates the location of the needle tip as determined by dissecting the phantom in the needle imaging plane.

FIG. 17A is the B-mode image, and FIG. 17B is the B-mode of FIG. 17A with needle visualization overlay. The "X" in each image indicates the location of the needle tip as determined by dissecting the phantom in the needle imaging plane.

FIGS. 18A and 18D show a 10 degree angle above the horizontal, FIGS. 18B and 18E show a 16 degree angle, and FIGS. 18C and 18F show a 32 degree angle. The "X" in each image of FIGS. 18D-18F illustrates the location of the needle tip as determined by dissecting the phantom in the needle imaging plane.

FIGS. 19A-19F are B-mode images of needles in degassed lean bovine muscle (FIGS. 19A-19C) and with needle visualization overlay applied (FIGS. 19D-19F). FIGS. 19A and 19D show a 21 G needle 0.75 mm elevationally off-axis from the transducer, FIGS. 19B and 19E show a 25 G needle 1.5 mm off-axis from the transducer, and FIGS. 19C and 19F show an on-axis 18 G needle at a 30-degree angle of insertion to the horizontal.

FIG. 20A shows the B-mode image, and FIG. 20B shows the needle overlay. Because these datasets were acquired after 2 cc of saline injection, it is likely that the decorrelation-removal step removed the area where the injectate had infiltrated.

FIG. 21A is a graph of RMS error of tip prediction versus elevation offset from the transducer. While measurements were acquired up to 4 mm offset from the transducer imaging plane, the distances shown are those that led to a generated needle tip prediction image.

FIG. 21B is a graph of the distribution of actual needle tip location versus needle tip prediction across all elevation offset distances in the lateral/axial plane for the three needle gauges. One can look at this plot as if the center of the plot is the needle tip and the locations of the needle tip predictions are shown as they were located with respect to the needle tip itself. The inner circle represents a 1.5 mm radius around the actual needle tip position and the arrows represent the mean tip prediction error for each needle gauge.

DETAILED DESCRIPTION OF EMBODIMENTS OF THE INVENTION

Figure 1:
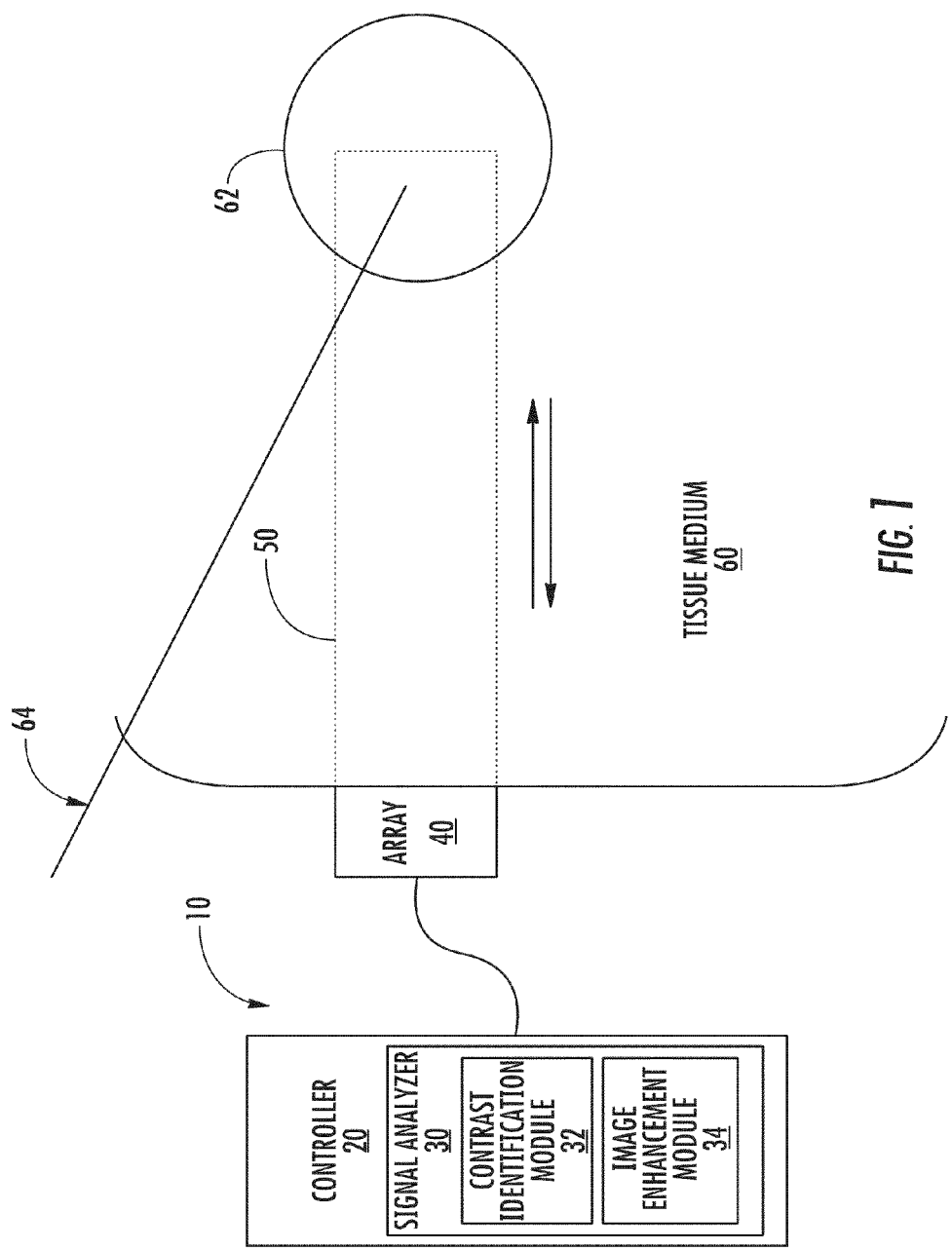
FIG. 1 is a schematic diagram of systems according to some embodiments of the invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As illustrated in FIG. 1, an ultrasound system 10 includes a controller 20, a signal analyzer 30 and an ultrasound transducer array 40. The ultrasound transducer array 40 is configured to transmit and receive ultrasound signals 50, and may be contacted to a target medium such as a tissue medium 60. As illustrated, the tissue medium 60 includes a target region 62 that can include a medical device, such as a needle 64. The signal analyzer 30 can include a contrast identification module 32 and an image data enhancement module 34.

Some embodiments of the current invention can be used with conventional B-mode ultrasound imaging data and/or acoustic radiation force imaging (ARFI) data. For example, the controller 20 and ultrasound array 40 can be configured to obtain conventional B-mode images and/or ARFI images in which the array 40 emits a series of low intensity "tracking lines" and higher intensity "pushing" pulses to interrogate the tissue medium 60. Various ultrasound techniques are described, for example, in U.S. Pat. Nos. 7,374,538 and 6,371,912, the disclosures of which are hereby incorporated by reference in their entireties. In some embodiments, B-mode and ARFI imaging data can be combined to provide a single image, and the medical device can be identified on the combined image. Moreover, two- or three-dimensional images can be used. It should also be understood that the ultrasound array 40 can be a one- or two-dimensional array having various numbers of ultrasound array elements.

Figure 2:
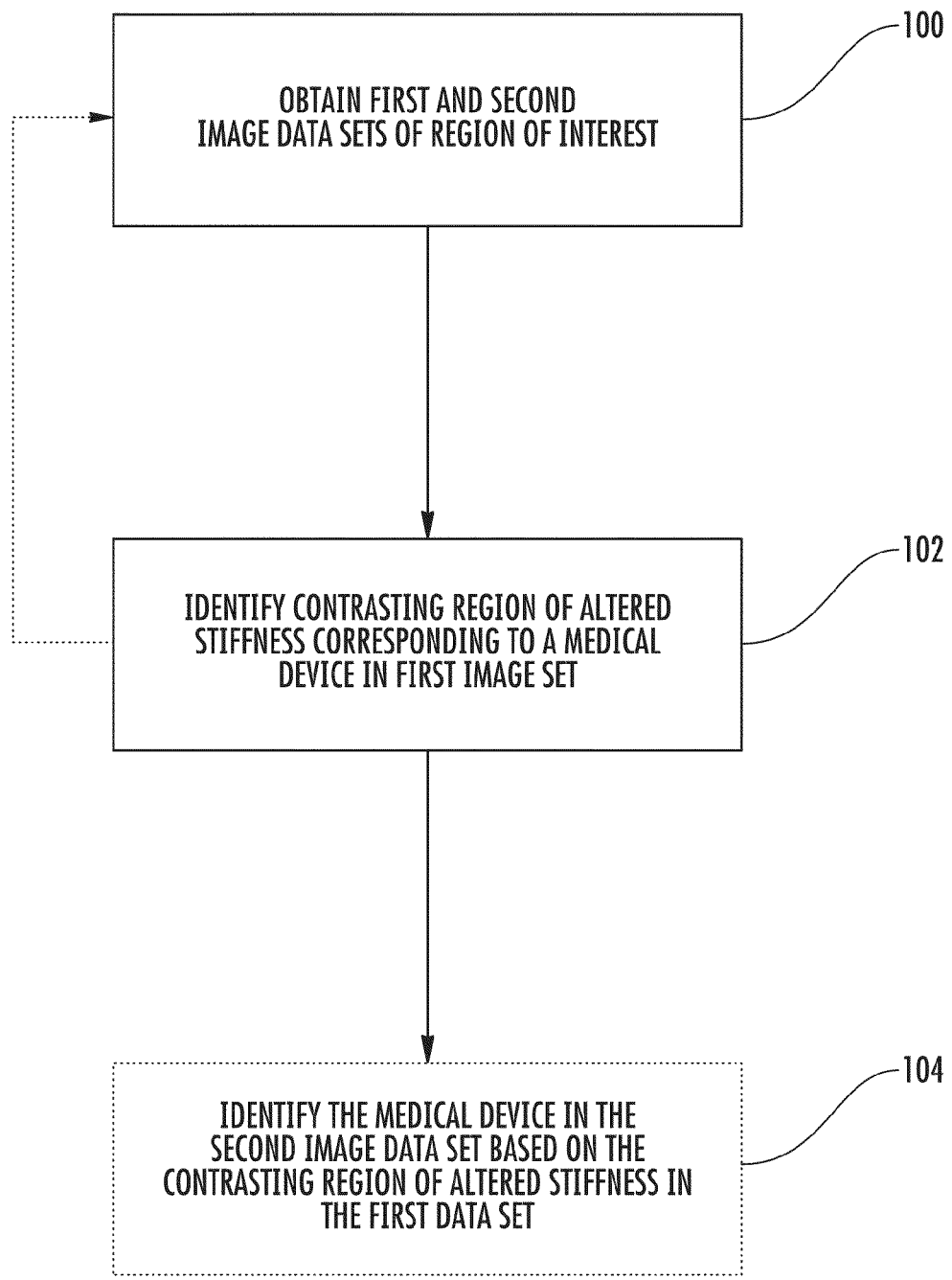
FIG. 2 is a flowchart of operations according to some embodiments of the invention.

In some embodiments, the ultrasound system 10 is configured to identify a presence of an object or medical device, such as a needle 64, in the target region 62. With reference to FIGS. 1 and 2 the signal analyzer 30 can acquire at least two image data sets of the region 62 from the ultrasound transducer array 40 (FIG. 2, Block 100). In some embodiments, the first image data set is an ARFI image data set and the second image data set is a B-mode ultrasound image data set. The contrast identification module 32 identifies a contrasting region of altered stiffness corresponding to an object, such as the needle 64, in the first image data set (FIG. 2, Block 102). The image data enhancement module 34 identifies the needle 64 in the second image data set based on the contrasting region of altered stiffness in the first image dataset (FIG. 2, Block 104).

In some embodiments, the first image data set is an ARFI image data set that can be used to provide improved visualization of areas of altered stiffness, such as for medical devices. However, clinicians may be more accustomed to B-mode images. The second image data set can be a B-mode image such that the region of increased stiffness in the ARFI image can be used to enhance the B-mode image. Portions of the ARFI image data set can be overlaid on a concurrently acquired image, such as a B-mode image, in order to provide enhanced visualization to the clinician in a B-mode image.

Figure 3:
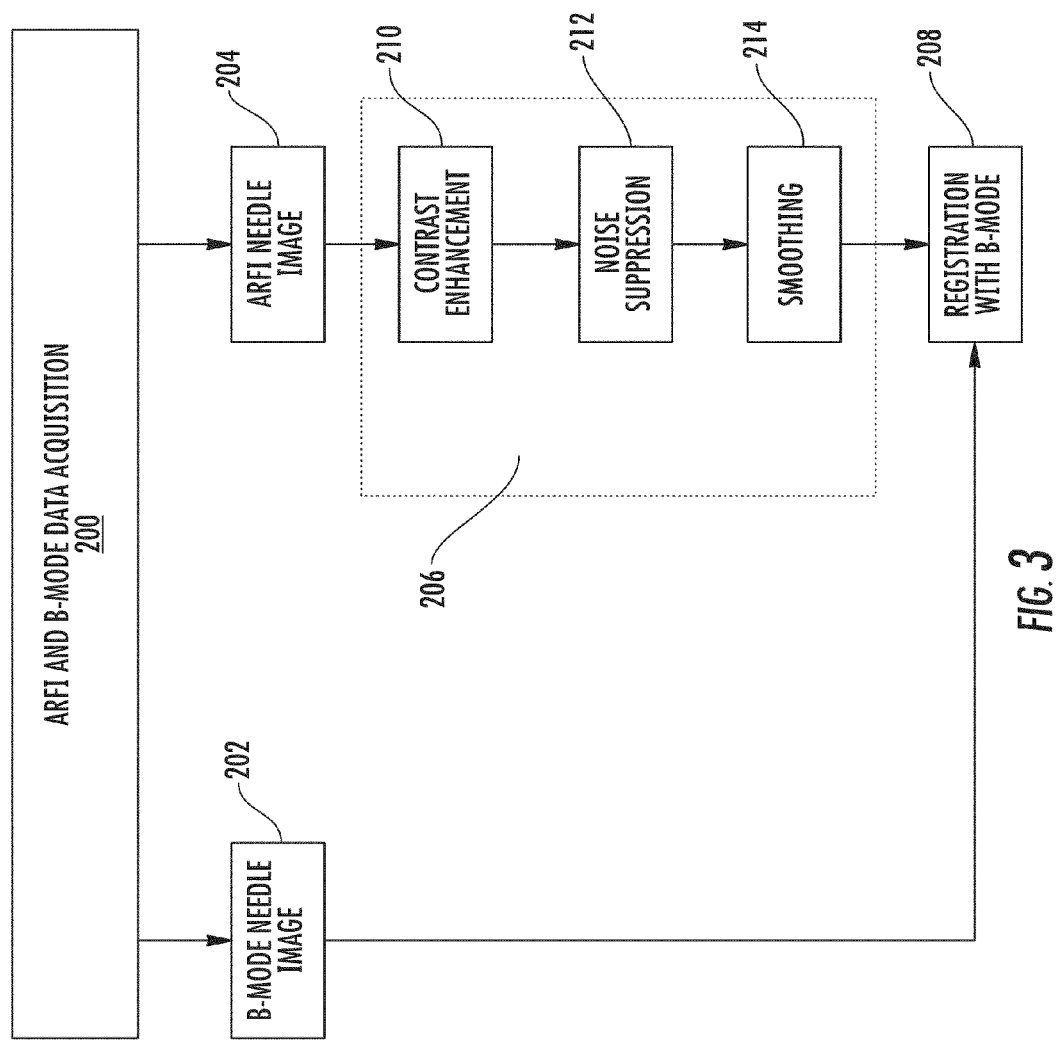
FIG. 3 is a flowchart of operations according to some embodiments of the invention.

Embodiments for enhancing an image of a needle are shown in FIG. 3. The ARFI and B-mode image data are acquired concurrently in an acquisition system (Block 200) to provide B-mode image data (Block 202) and ARFI image data (Block 204). The needle (or a portion of the needle, such as the tip portion) is identified in the ARFI image data, for example, using image segmentation techniques, at Block 206 based on a region of altered stiffness. At Block 208, the region of altered stiffness corresponding to the needle that is obtained from the ARFI image data set in Block 206 is registered or combined with the B-mode image data set.

Accordingly, the identified region of altered stiffness can be visually identified in the B-mode image. In some embodiments, the region of altered stiffness is registered with the B-mode image by overlaying at least a portion of the ARFI image on the B-mode image. However, other techniques for combining the ARFI image data set and the B-mode image data set can be used as discussed herein. For example, pixels in the B-mode image that correspond to the region of altered stiffness in the ARFI image data set can be identified and visually altered, for example, using color and/or brightness contrast. In some embodiments, known characteristics of the object that is identified in the ARFI image can be used to enhance the image. For example, if the object is a straight needle, the region of altered stiffness obtained with the B-mode image can be analyzed based on the known shape of the needle, e.g., to smooth and/or straighten a representation of the region of altered stiffness to conform to the straight shape of the needle.

Exemplary calculations for identifying a needle using a combined ARFI and B-Mode image data according to some embodiments of the invention are described below with reference to FIG. 3.

Image Segmentation (Block 206 (FIG. 3))

The image segmentation calculation developed to create a computerized needle position estimate from ARFI images contains three steps: contrast enhancement (Block 210; FIG. 3), noise suppression (Block 212; FIG. 3), and smoothing with edge preservation (Block 213; FIG. 3). The needle location prediction derived from the ARFI image is then overlaid on the concurrently acquired B-mode image for easier clinician visualization.

Contrast Enhancement (Block 210 (FIG. 3))

Ultrasound images, and in particular, B-mode ultrasound images, may be susceptible to speckle variations that do not make them amenable to edge detection by conventional means. S. Pathak, V. Chalana, D. Haynor, and Y. Kim, "Edge-guided boundary delineation in prostate ultrasound images," *IEEE Transactions on Medical Imaging*, vol. 19, no. 12, pp. 1211-1219, 2000. While ARFI images do not contain the same sources of speckle, identification of the needle can be confused by irregularities in the underlying tissue structure. Theories applied to this imaging question may include modified approaches from other imaging modalities, particularly in the two-part contrast enhancement step: image normalization and application of a Laplacian operator for edge detection. FIGS. 4A-4D provide images demonstrating the steps outlined below. Although embodiments according to the present invention are described herein with respect to exemplary image normalization and edge detection techniques, it should be understood that other normalization and edge detection techniques may be used. For example, any suitable computational edge detector can be used in addition to the Laplacian operator, such as the Canny operator, the Sobel operator and others. Exemplary image normalization and edge detection using Laplacian operators will now be described.

Image Normalization: Initial needle contrast enhancement was performed through image normalization, which was applied to account for the depth-dependent focal gain associated with the applied radiation force. This force creates spatial gradients in ARFI displacement images of homogenous tissues, with more complex displacement images occurring in heterogeneous tissues, and leads to decreased displacement measurements away from the focus and with increasing depth. M. Palmeri, A. Sharma, R. Bouchard, R. Nightingale, and K. Nightingale, "A finite element model of soft tissue response to impulsive acoustic radiation force," *IEEE Trans Ultrason Ferroelec Freq Control*, vol. 52, no. 10, pp. 1699-1712, 2005. Thus, the ARFI needle image was normalized by depth using an average of 20 reference lines in the far left of the image where there was no needle (see FIGS. 4A-4D). This process is analogous to temporal gain control, or TGC, for B-mode, in which a gain factor is calculated for every depth to normalize the image based on attenuation of the ultrasound signal. D. Hughes and F. Duck, "Automatic attenuation compensation for ultrasonic imaging," *Ultrasound in Medicine and Biology*, vol. 23, no. 5, pp. 651-664, 1997.

Laplacian Operator: In ARFI images, needles are visible with a high degree of contrast, so smoothing is performed prior to edge detection. Typically, in B-mode segmentation, the Laplacian-of-Gaussian (LoG) method is used, which involves Laplacian filtration of a Gaussian-filtered image for noise reduction. X. Wang, "Laplacian operator-based edge detectors," *IEEE Transactions on Pattern Analysis and Machine Intelligence*, vol. 29, pp. 886-890, 2007. In this work, a median filter (rather than a Gaussian filter) was used prior to the Laplacian operator because it is particularly effective in reduction of "salt-and-pepper" noise without removing image details, thereby preserving contrast between the needle and surrounding tissue while attenuating the subtle noise (or jitter) and slight mechanical inhomogeneities of the tissue in the ARFI image. R. Jain, R. Kasturi, and R. Schunck, *Machine Vision*. P.O. Box 182604, Columbus, Ohio 43272: McGraw-Hill, Inc., 1995. The spatial dimensions of the median filter were 1.73 mm in the axial dimension and 0.88 mm in the lateral dimension, as determined empirically through testing with a subset of 10 ARFI needle images.

The Laplacian operator applied to the normalized and median-filtered image is the two-dimensional equivalent of the second derivative, which is used to find the local maxima in gradient values (areas of highest contrast) by finding the zero crossing of the second derivative. The formula for the Laplacian of a function $f(x,y)$, is (see R. Jain, R. Kasturi, and R. Schunck, *Machine Vision*. P.O. Box 182604, Columbus, Ohio 43272: McGraw-Hill, Inc., 1995.):

$$\nabla^2 f = \frac{\partial^2 f}{\partial x^2} + \frac{\partial^2 f}{\partial y^2} \tag{1}$$

The second derivatives along the x and y direction are approximated using difference equations as follows:

$$\frac{\partial^2 f}{\partial x^2} = f[i, j+1] - 2f[i, j] + f[i, j-1] \tag{2}$$

$$\frac{\partial^2 f}{\partial y^2} = f[i+1, j] - 2f[i, j] + f[i-1, j] \tag{3}$$

In image processing, these difference equations can be approximated as a mask:

$$\nabla^2 = \begin{vmatrix} 0 & 1 & 0 \\ 1 & -4 & 1 \\ 0 & 1 & 0 \end{vmatrix} \tag{4}$$

An adapted negative Laplacian mask was used as implemented in MATLAB (MathWorks™, Novi, Mich.) to further emphasize the center pixel and areas of high contrast (see R.

Jain, R. Kasturi, and R. Schunck, *Machine Vision*. P.O. Box 182604, Columbus, Ohio 43272: McGraw-Hill, Inc., 1995.):

$$\nabla^2 = 0.8 * \begin{vmatrix} -0.2 & -0.8 & -0.2 \\ -0.8 & 5.2 & -0.8 \\ -0.2 & -0.8 & -0.2 \end{vmatrix} \quad (5)$$

After taking the Laplacian of the median filtered and normalized ARFI displacement image, a global contrast threshold was applied in order to select regions of higher contrast:

$$\Phi = \frac{\mu_1 = \mu_2}{2} \quad (6)$$

In equation 6, $\Phi$ is the threshold value, and $\mu_1$ and $\mu_2$ are the mean contrast values inside and outside of the needle, respectively. The threshold was determined through manual identification of the needle in an on-axis B-mode image and finding the mean contrast value inside and out of the needle in a test set of 16 ARFI images per needle gauge. Regions in which Laplacian operator contrast output was lower than $\Phi$ were removed from the needle image before further processing.

A different contrast threshold was determined for the three needle gauges: 0.8 for the 18 G needles, 0.5 for the 21 G needles, and 0.5 for the 25 G needles.

Noise Suppression (Block 212 (FIG. 3))

Noise reduction methods for ultrasound images frequently rely on low-pass filters such as the mean or median filter; however, if the filter window is particularly large these can often blur the edges. R. Jain, R. Kasturi, and R. Schunck, *Machine Vision*. P.O. Box 182604, Columbus, Ohio 43272: McGraw-Hill, Inc., 1995; A. Jain, *Fundamentals of Digital Image Processing*. New Jersey: Prentice-Hall, 1989; C. Chinrungrueng and A. Suvichakorn, "Fast edge-preserving noise reduction for ultrasound images," *IEEE Transactions on Nuclear Science*, vol. 48, no. 3, pp. 849-854, 2001. More targeted approaches that can maintain important information include frame-to-frame cross correlation calculation. G. Trahey, J. Allison, and O. VonRamm, "Angle independent ultrasonic detection of blood flow," *IEEE BME*, vol. BME-34, no. 12, pp. 965-967, 1987. M. Palmeri, S. McAleavey, a Trahey, and K. Nightingale, "Ultrasonic tracking of acoustic radiation force-induced displacements in homogeneous media," *IEEE Trans Ultras Ferroelec Freq Control*, vol. 53, no. 7, pp. 1300-1313, 2006. In ARFI data, displacements are estimated using correlation based methods. The correlation coefficients can thus be used to eliminate poor displacement estimates that can result from jitter, reverberations, and air in the sample. Regions with low cross-correlation coefficients as calculated during ARFI displacement estimation were removed from the needle prediction image with a correlation cutoff set at 0.999. Removal of poor displacement estimates is computationally faster at this step in the process because a binary image is created with the contrast threshold. Thus, the poorly correlated areas can be assigned a background pixel value of zero rather than finding nearest neighbors to fill in poor estimates, which can be a computationally time-intensive process.

Smoothing/Continuity Constraint (Block 214 (FIG. 3))

Figure 5A:
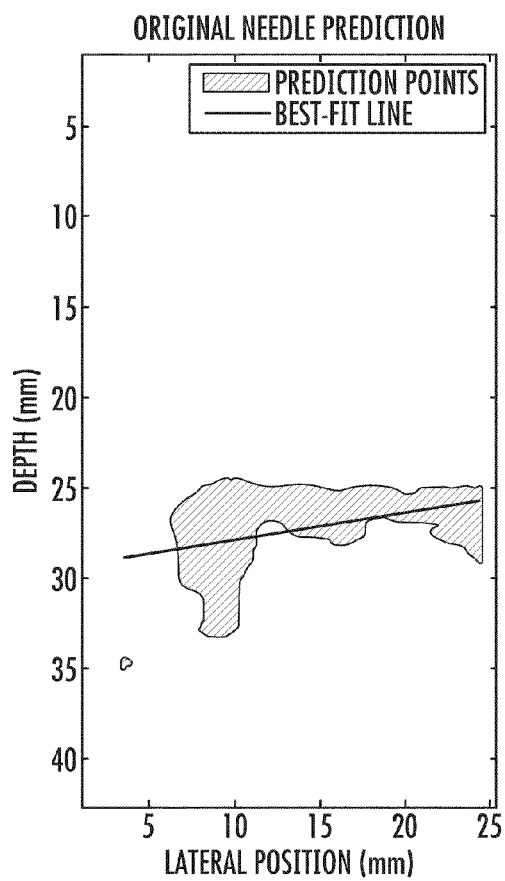
FIGS. 5A-5B are graphs of the lateral position of a needle as a function of depth and illustrate the smoothing of binary needle prediction images through an application of continuity constraint(s) according to some embodiments of the invention.
Figure 5B:
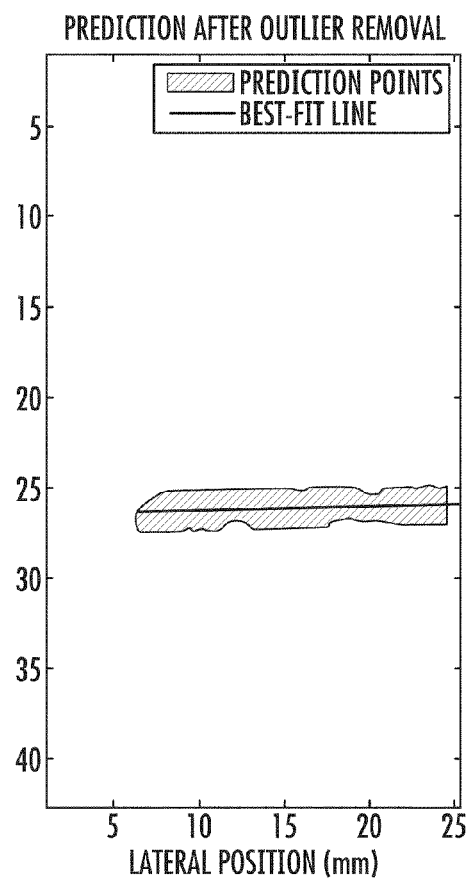

Because needles are rigid bodies, one can use a priori knowledge of needle shape to generate a physically realistic image from acquired data. In the case of needles and other linear objects, a simple way to perform smoothing involves fitting a line through the high contrast points predicted from the threshold image. For this application, the binary prediction images as shown in FIG. 4D were subjected to a continuity constraint in the form of a best-fit line prediction. This best-fit line used the lateral tip location predicted by previous steps followed by an iterative removal of outliers to predict the axial needle location. The iterative removal of outliers continued until 25% of the outliers from the original prediction image were removed by recursively removing the point farthest from each successive best-fit line prediction, termed the residual point. The improvement in needle prediction image is shown in FIGS. 5A-5B. In FIG. 5A, the binary prediction output from a contrast enhancement and noise reduction step is subject to a continuity constraint line of best-fit without removal of outliers. In FIG. 5B, the best-fit line is shown through the needle prediction points after the iterative removal of oulier points. FIGS. 5A-5B are images of an 18 G needle 2.24 mm off-axis in elevation from the transducer imaging plane.

The needle width displayed in the overlayed needle images represents the axial standard deviation of the needle prediction points after iterative outlier removal.

Some embodiments according to the present invention will now be discussed with respect to the following non-limiting examples.

EXAMPLE 1

Experimental Setup

Figure 6A:
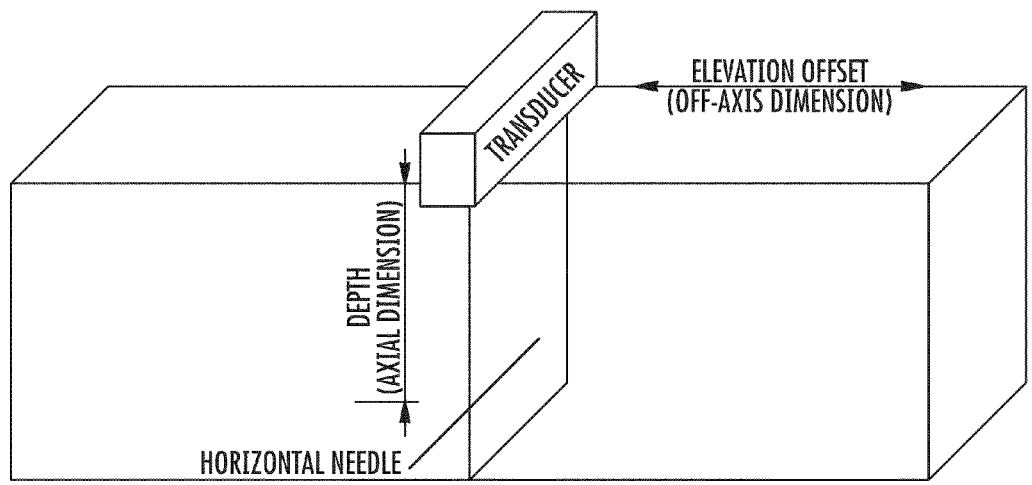
FIG. 6A is a diagram illustrating transducer placement for horizontal needle acquisitions according to some embodiments of the present invention.
Figure 6B:
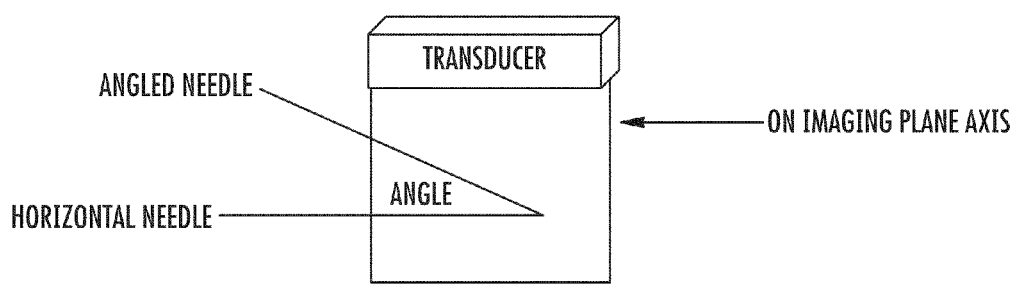
FIG. 6B is a diagram illustrating transducer placement for angled needle acquisitions according to some embodiments of the present invention.

Lean bovine muscle in degassed and deionized water was used for the experiments. 18 G, 21 G and 25 G (Becton Dickinson and Company, Franklin Lakes, N.J.) needles were then imaged in two configurations: horizontal longitudinally, and at multiple angles to the horizontal. The horizontal longitudinal images were taken both on-axis and in fixed elevation increments off-axis to the transducer imaging plane. A diagram of the experimental setup is shown in FIGS. 6A-6B.

Experiments were performed with a Siemens SONOLINE™ Antares scanner with a VF7-3 transducer (Siemens Medical Systems, Ultrasound Group, Issaquah, Wash., USA). The system has been modified for user control of acoustic beam sequences and intensities, as well as allowing access to the in-phase and quadrature (IQ) data, A Daedal Positioning Systems model 2525 rotatory positioning stage (Parker Hannifin Corp, Daedal Division, Irwin, Pa.) with a custom attachment was used to measure the angle of needle insertion to the horizontal. Two ultrasonic imaging processes were used in this experiment: conventional B-mode, and ARFI imaging. Two types of acoustic beams are used to generate ARFI displacement images: high intensity pushing beams and conventional B-mode tracking beams M. Palmeri, S. McAleavey, G. Trahey, and K. Nightingale, "Ultrasonic tracking of acoustic radiation force-induced displacements in homogeneous media," *IEEE Trans Ultras Ferroelec Freq Control*, vol. 53, no. 7, pp. 1300-1313, 2006; M. Palmeri, *Imaging the mechanical properties of tissue with ultrasound: An investigation of the response of soft tissue to acoustic radiation force*. PhD thesis, Duke University, 2005; K. Nightingale, M. Soo, M. Palmeri, A. Congdon, K. Frinkley, and G. Trahey, "Imaging tissue mechanical properties using impulsive acoustic radiation force," in *IEEE Biomedical Imaging Symposium*, no. 1, pp. 41-44, 2004. The beams were created by a Siemens VF7-3 linear array (5.33 MHz center frequency), and were electronically laterally focused at 25 mm, with an F/2 focal configuration, and had a fixed elevation focus near 37.5 mm unless otherwise specified. To generate an ARFI image, a reference tracking beam is fired, followed by a pushing beam. The pushing beams are similar to color Doppler pulses, but with unapodized apertures and longer pulse lengths (400 cycles) for a duration of 95 μs. The pushing beam was followed by a series of 50 tracking beams in typical A-line configuration fired at a pulse repetition frequency (PRF) of 7 kHz for an overall tracking duration of up to 7 msec in each pushing location. The lateral field of view was 25 mm, obtained with 36 pushing locations and 4 parallel receive tracking beams with uniform lateral spacing.

The transducer was held with a motorized translation stage (model NM 3000, 0.1 μm precision, Newport Corporation, Irvine, Calif.). The custom pulse sequence was fired, and IQ data were stored for off-line processing. An additional B-mode image was stored as well for comparison with the ARFI data and registration. Local displacement estimates were acquired using the Loupas phase-shift estimator (see T. Loupas, R. Peterson, and R. Gill, "Experimental evaluation of velocity and power estimation for ultrasound blood flow imaging, by means of a two-dimensional autocorrelation approach," *IEEE Trans Ultras Ferroelec Freq Control*, vol. 42, pp. 689-699, 1995. G. Pinton, J. Dahl, and G. Trahey, "Rapid tracking of small displacements with ultrasound," *IEEE Trans Ultrason Ferroelec Freq Control*, vol. 53, no. 6, pp. 1103-1117, 2006.) and 1-D cross correlation between sequentially acquired tracking lines. G. Trahey, J. Allison, and O. VonRamm, "Angle independent ultrasonic detection of blood flow," *IEEE BME*, vol. BME-34, no. 12, pp. 965-967, 1987. The complete ARFI dataset yields displacement estimates through time for a 2-D region of interest. K. Nightingale, M. Palmeri, and G. Trahey, "Analysis of M. Palmeri, *Imaging the mechanical properties of tissue with ultrasound: An investigation of the response of soft tissue to acoustic radiation force*. PhD thesis, Duke University, 2005," 2005.

Needle Visualization Implementation

The needle visualization techniques described herein were applied to datasets obtained using horizontal 18, 21, and 25 gauge needles at 16 locations on and elevationally off-axis to the transducer in 0.25 mm increments, and to needles on the transducer axis between 5 and 30 degrees to the horizontal, as shown in FIGS. 6A-6B. The enhanced-visualized needle was compared to the original ARFI images as well as the B-mode images. While many existing ultrasound segmentation techniques require user input, the needle visualization techniques described herein may be fully automated based on underlying features of the ARFI image. The contrast threshold was based on the assumption a near-gaussian distribution of pixel values inside and outside the needle to generate a fixed global contrast threshold for each needle gauge. R. Gonzalez and R. Woods, *Digital Image Processing*. New Jersey: Prentice-Hall, 2001. In order to ensure automaticity, the contrast threshold was not adjusted in the remaining testing of the technique. The preset contrast, correlation coefficient cutoff, and smoothing functions can be implemented such that real-time user input is not required.

Registration with B-mode (Block 208 (FIG. 3))

Image registration as used herein refers to the construction of a composite medical image from overlapping images. Often, this process involves a linear transformation between two images or portions of two images. It should be understood that image registration can also include other image processing techniques, for example, to address any irregularities or skewing of the images. M. Thomas, M. Joachim, V. Hans, and G. Maggie, "Medical image processing toolbox in Matlab: Registration, masters thesis," *University College of Antwerpen, Belgium*, 2006. Image matching has previously been accomplished between ARFI and B-mode images acquired using the same transducer. K. Nightingale, M. Palmeri, and G. Trahey, "Analysis of contrast in images generated with transient acoustic radiation force," *Ultrasound Med. Biol.*, vol. 32, no. 1, pp. 61-72, 2006. For the needle and B-mode images, the registration process was a linear scaling transformation between the binary needle image mask created from the ARFI data and the B-mode image. Since both were acquired in the same configuration with the same transducer, the registration process required no further transformations and the data were exactly matched in lateral and axial position. The needle prediction output of the segmentation calculation was turned into a mask for the existing B-mode image without needing modifications. Depending on clinician preference, the mask can be opaque or transparent, and can allow the clinician to view the needle relative to familiar B-mode landmarks. The needle was displayed in the registered image as having the radius equal to the axial standard deviation of the needle prediction points.

Needle Tip Localization

Figure 7:
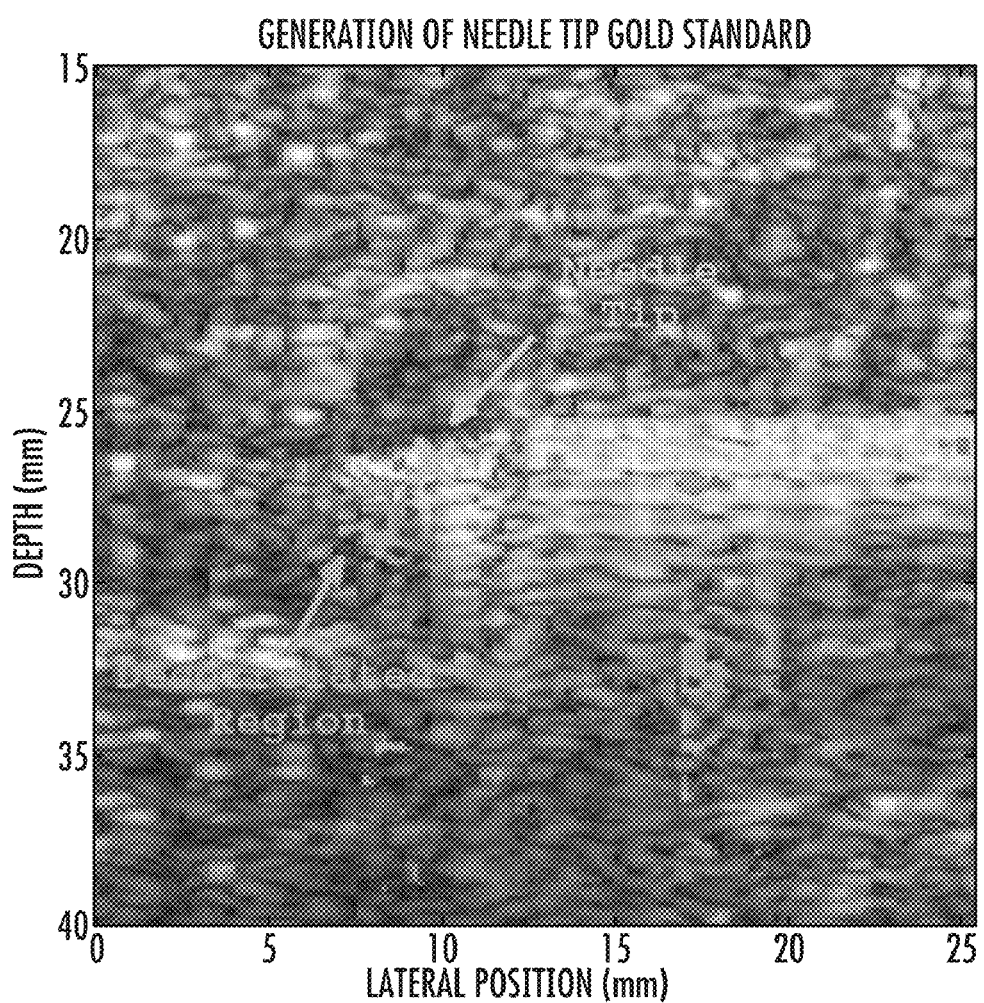
FIG. 7 is a graph of B-mode image data in which the needle tip is identified in on-axis B-mode images through removal of decorrelated regions likely to be air bubbles introduced by needle insertion.

Visualization of the needle tip may be particularly important for clinical applications to identify where surrounding anatomical structures are located in comparison to the needle. In order to perform a quantitave evaluation of the accuracy of the ARFI-based needle segmentation calculation, the needle tip location had to be verified. This was done by evaluation of the B-mode image of the on-axis needle data acquisition for each dataset. In some cases, air was introduced during needle introduction and the tip location was difficult to distinguish from the air in B-mode. Air introduces jitter that will not yield consistent ARFI displacement values between frames of displacement image acquisition, causing the correlation coefficient as calculated in the data preprocessing step to be lower in regions that have air bubbles than in the surrounding tissue. G. Trahey, J. Allison, and a VonRamm, "Angle independent ultrasonic detection of blood flow," *IEEE BME*, vol. BME-34, no. 12, pp. 965-967, 1987. A decorrelation map was generated by displaying all areas of the ARFI image that had lower correlation coefficients than a threshold, set at 0.99. S. McAleavey, K. Nightingale, and G. Trahey, "Estimates of echo correlation and measurement bias in acoustic radiation force impulse imaging," *IEEE Trans Ultras Ferroelec Freq Control*, vol. 50, no. 6, pp. 631-641, 2003. This map was displayed as a contrasting overlay on the on-axis B-mode image as shown in FIG. 7. Other sources of decorrelation include frame-to-frame movement and jitter. The regular patterns of decorrelation below the needle in this image also suggest reverberations within the needle. The "X" marks the identified needle tip location as determined by following the upper edge of the needle in the B-mode image down the bevel until it is interrupted by a decorrelated region, likely representing an air bubble. This approach was validated by real-time B-mode imaging of the needle tip motion.

As seen in FIG. 7 with the regular pattern of decorrelation below the needle, reverberations of acoustic energy within the needle as well as other jitter-like movement can be sources of low correlation coefficients as represented by the contrasting mask. The needle tip position was found by following the upper edge of the needle as it appeared in B-mode because this is the first acoustic echo from the needle points, and following the needle down the bevel (which was always oriented toward the top of the image in the experimental acquisitions to provide the best needle tip visibility in B-mode images. See R. Hopkins and M. Bradley, "In-vitro visualization of biopsy needles with ultrasound: A comparative study of standard and echogenic needles using an ultrasound phantom," *Clinical Radiology*, vol. 56, pp. 499-502, 2001) until reaching the decorrelated region which represented air bubbles at the tip. The accuracy of this method was confirmed by inserting 18 G, 21 G, and 25 G needles into lean bovine muscle and moving the tip in a real-time on-axis B-mode image to identify needle tip location as is usually done in the clinic. This agreed with the manual tip identification in B-mode after removal of decorrelated regions to within a 1 mm radius.

Results:

Exemplary overlaid binary needle images with co-registered B-mode images are shown in FIGS. 8A-8F for various elevation offsets between the horizontal needle and transducer imaging plane. FIGS. 9A-9B provides exemplary images with a smaller (25 G) needle. The calculation was also applied to needles at angles on-axis, as shown in FIGS. 10 and 11.

Needle tip prediction accuracy is particularly important for clinical applications especially influencing success rate of intravenous catheterization and regional anesthesia and avoidance of damage to surrounding tissue structures. The difference between the needle tip prediction calculation output and the actual needle tip location can be viewed in the form of a polar plot. FIG. 12B shows the overall distances and angles between the estimated needle tip location in the axial/lateral plane and the actual needle tip location for the three needle gauges with the actual tip position being located at the center of the plot. The root-mean-square (RMS) distance between the tip prediction and actual tip location as a function of to elevation offset from the transducer are shown in FIG. 12A. FIGS. 13A-13B show the differences between needle tip prediction and needle tip location for the 18 G needles inserted at various angles to the horizontal.

In clinical settings, where a nerve or vessel has been visualized with B-mode but the needle cannot be well-visualized, embodiments according to the invention may be implemented for the clinician to determine the needle location. The accuracy of needle tip prediction as described herein suggests that implementation would be a clinically useful tool. As shown in FIGS. 12A-12B, the calculation performs particularly well with elevation offsets between 1 mm and 3 mm, where the needle tip prediction is likely to be within 1.5 mm of the actual needle tip location. The needle prediction calculation also performed to within 2 mm of the actual needle tip close to the transducer imaging plane axis in the 18 G and 25 G cases. While the 21 G needle tip prediction does not perform as well closer to the axis of the transducer imaging plane, B-mode imaging works well close to the imaging plane axis, so this does not present a barrier to clinical applicability for the calculation. In cases where the needle cannot be visualized with B-mode (an offset greater than 1 mm from the transducer), the ARFI image enhanced needle tip estimate is likely to be within 1.5 mm of the actual needle tip, as seen in FIGS. 12A-12B.

Figure 11A:
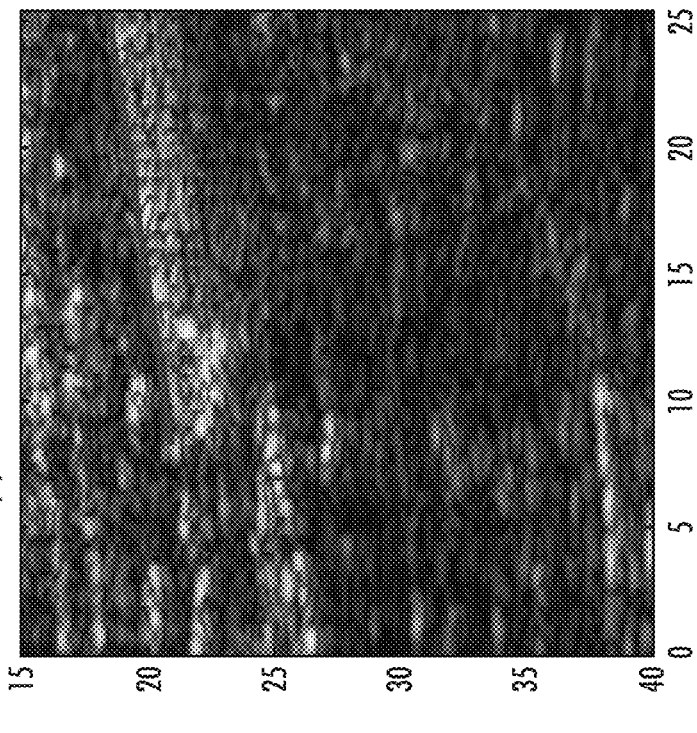
FIG. 11A is a B-mode image of an 18 G needle at 30 degrees from the horizontal with respect to the transducer in lean bovine muscle.
Figure 11B:
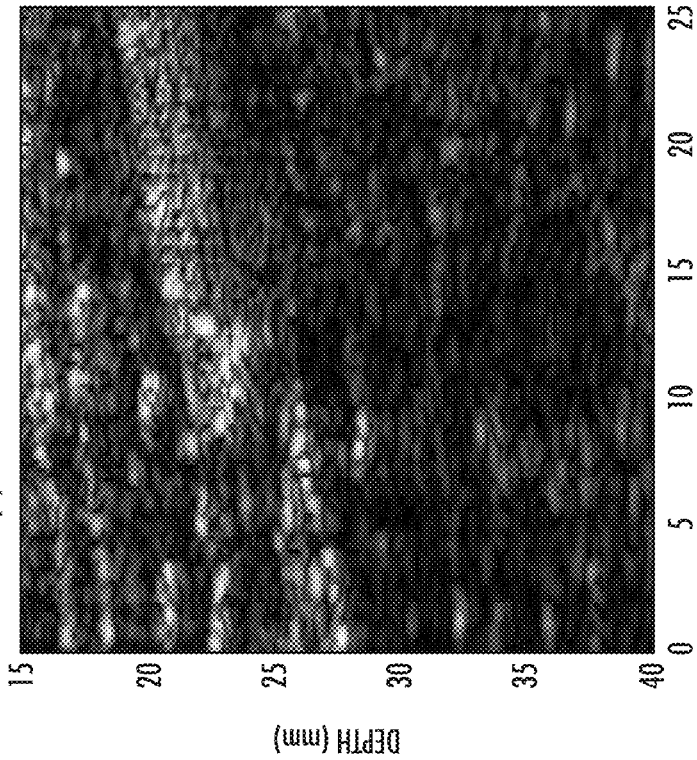
FIG. 11B is the B-mode image of FIG. 11A with a region of increased stiffness from a corresponding ARFI image overlay to enhance the needle location.

While the needle tip prediction is close to the actual needle tip location in the axial/lateral plane, the elevation offset from the transducer imaging plane in which the prediction outputs a needle estimate could impose a needle tip interpretation error. For the applications to regional anesthesia and central venous access, however, the important information for the clinician is knowledge of where the needle tip is relative to other structures in the B-mode. Having a needle tip identification calculation that can tell the clinician that the needle is close to a desired anatomic detail of interest (such as a nerve or vessel) will allow the clinician to easily shift the transducer to an on-axis view in which a nerve and needle can be visualized together in the B-mode image. In addition, the needle tip prediction estimates differed from the actual needle tip location as the needle and imaging plane axis became more misaligned. As shown in FIGS. 12A-12B, the needle tip prediction began to deviate from the actual needle tip when the elevation misalignment between the needle and imaging plane axis approached 3 mm. The stiff immobile needle reduces the motion of the surrounding tissue, causing a radius of lower displacements than the surrounding tissue as seen in the ARFI displacement images. This radius of decreased displacement explains the fact that the needle can be seen well in ARFI displacement images up to 3 mm away from the transducer imaging plane. As the needle moves even farther out of plane, as evidenced in the 4 mm off-axis case for the 21 G needle, the needle prediction calculation ceases to output a needle prediction at all, because there is no longer enough contrast in the ARFI image. Thus, while the needle prediction calculation does not offer accurate predictions of needle tip location greater than 3 mm off-axis in elevation to the transducer imaging plane, it effectively doubles the needle visualization as compared to B-mode. Visualization of angled needles is an important aspect of central venous catheter insertion and regional anesthesia due to requirements from anatomic structure location and difficulties in seeing angled needles with B-mode. A. Gray, "Ultrasound-guided regional anesthesia," *Anesthesiology*, vol. 104, no. 2, pp. 368-373, 2006. As shown in FIGS. 8A-8F and FIGS. 9A-9B, the needle visualization calculation can improve visualization of angled needles over B-mode, particularly in the steeper 30 degree angle case. In addition, although the B-mode of the 5-degree angled needle shows a significant amount of reverberation, the needle prediction image is tied to the upper boundary of the needle in the B-mode image, demonstrating that the ARFI-based calculation is not as susceptible to reverberations as the B-mode image, as seen in FIGS. 11A-11B. FIGS. 13A-13B show the needle tip prediction error as compared to manual tip identification using decorrelation maps for angled needles. All tip predictions performed as well as the 18 G on-axis needle prediction shown in FIGS. 12A-12B. Accordingly, the angled needle prediction images improve needle visualization over B-mode, which is an improvement which may greatly aid ultrasound-guided anesthesia and central venous catheter placement.

EXAMPLE 2

Figure 14B:
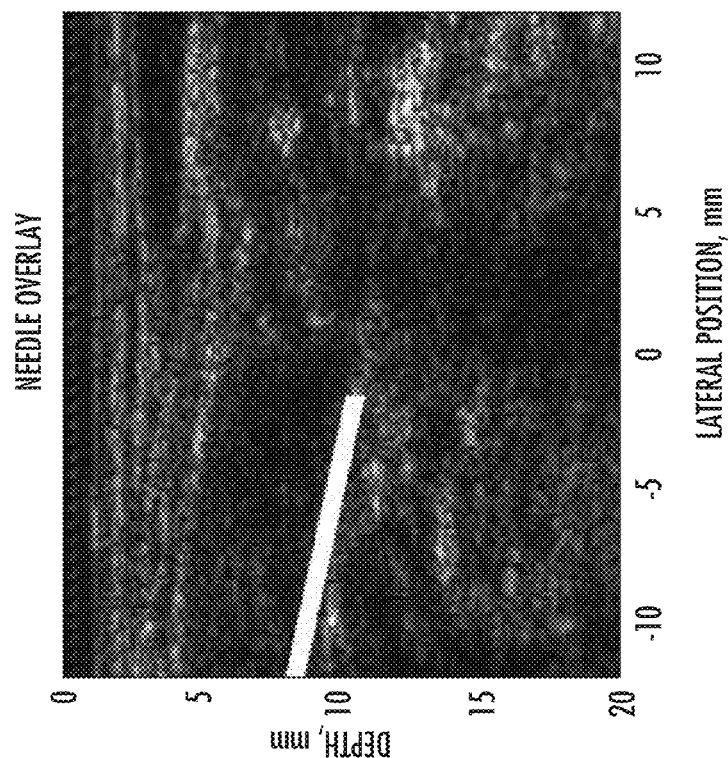
FIG. 14B is the B-mode image of FIG. 14A with an ARFI image data overlay to identify the needle position.
Figure 14A:
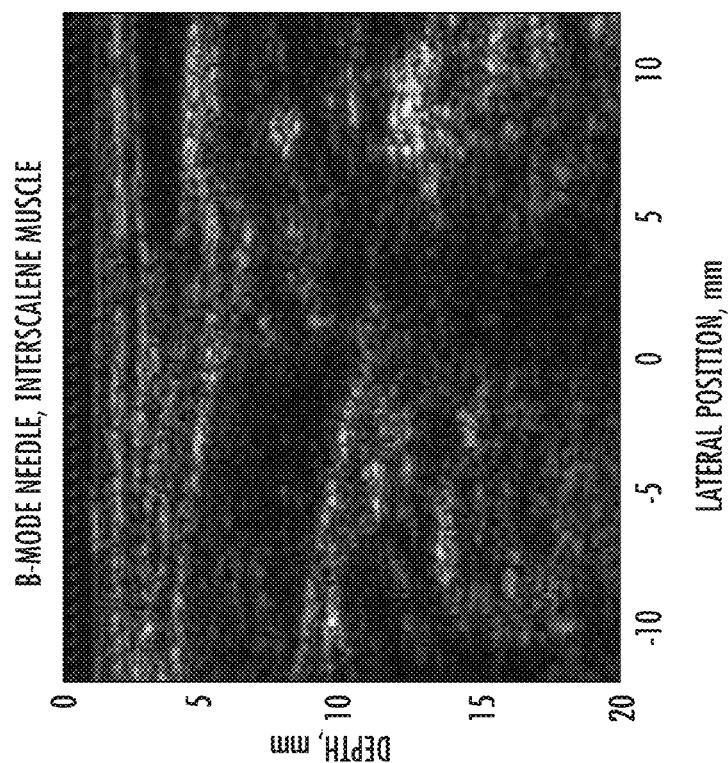
FIG. 14A is a B-mode image of an in vivo needle in the tissue of a human subject.
Figure 16A:
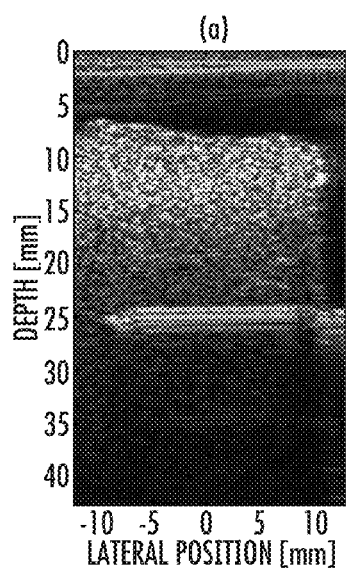
FIGS. 16A-F are B-mode images of a horizontal 21 G needle in a 200-bloom graphite phantom at several locations elevationally off-axis from the transducer without (FIGS. 16A-16C) and with (FIGS. 16D-16F) needle visualization algorithm applied.
Figure 16B:
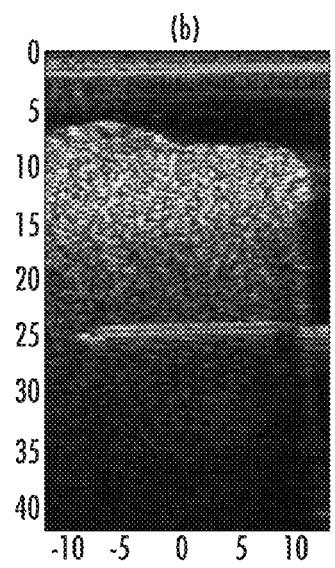
Figure 16C:
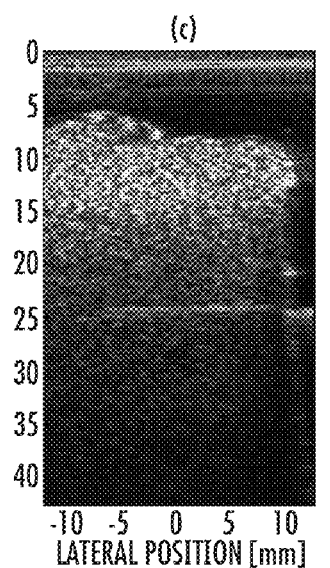
Figure 16D:
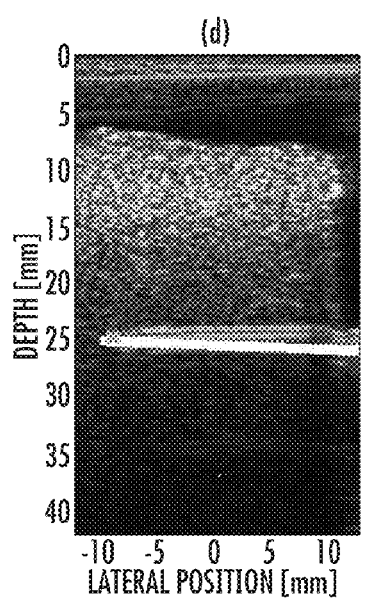
Figure 16E:
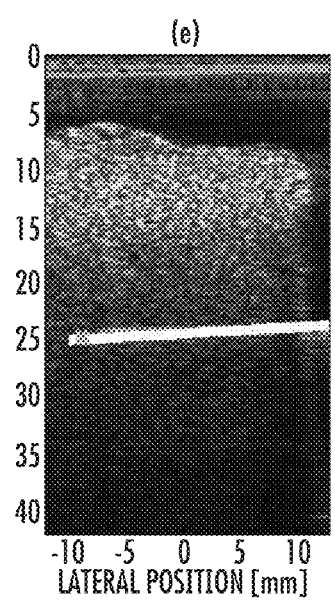
Figure 16F:
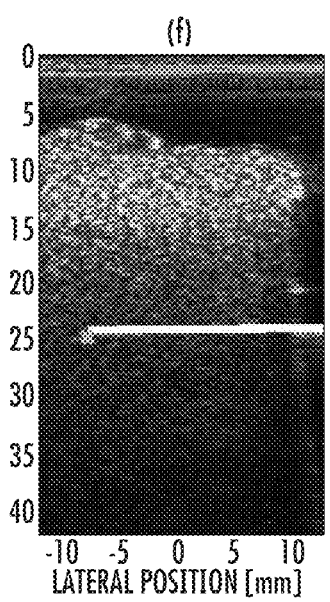

FIGS. 14A-14B are in vivo images of a needle in a human subject in which a right interscalene after 2 mL of saline injection is shown. FIG. 14A is a B-mode image, and FIG. 14B is the B-mode image of FIG. 14A with an ARFI image data overlay to identify the needle position.

EXAMPLE 3

Experimental Setup

Two-hundred bloom graphite tissue-mimicking phantoms were used throughout the experiment. The fabrication procedures for these phantoms are outlined in M. Palmeri, A. Sharma, R. Bouchard, R. Nightingale, and K. Nightingale, "A finite element model of soft tissue response to impulsive acoustic radiation force," *IEEE Trans Ultrason Ferroelec Freq Control*, vol. 52, no. 10, pp. 1699-1712, 2005 and T. Hall, M. Bilgen, M. Insana, and P. Chaturvedi, "Phantoms for elastography," in *Proceedings of the 1996 Ultrasonics Symposium*, pp. 1193-1196, 1996. Eighteen gauge, twenty-one gauge and twenty-five gauge (Becton Dickinson and Company, Franklin Lakes, N.J.) needles (outside diameters 1.27 mm, 0.82 mm, 0.52 mm respectively) were then imaged in two configurations: horizontal longitudinally. The 18 G needles were examined at multiple angles to the horizontal. The horizontal longitudinal images were taken both on-axis and in fixed elevation increments off-axis to the transducer imaging plane. A diagram of the experimental setup is shown in FIGS. 6A-6B. In addition, datasets were acquired in degassed lean bovine muscle and during one in vivo brachial plexus injection experiment to examine the effectiveness of the technique. An in vivo dataset was acquired in a 39-year old male. Experiments were performed with a Siemens SONOLINE™ Antares scanner with a VF7-3 transducer (Siemens Medical Systems, Ultrasound Group, Issaquah, Wash., USA). The system has been modified for user control of acoustic beam sequences and intensities, as well as allowing access to the in-phase and quadrature (IQ) data. See G. Pinton, J. Dahl, and G. Trahey, "Rapid tracking of small displacements with ultrasound," *IEEE Trans Ultrason Ferroelec Freq Control*, vol. 53, no. 6, pp. 1103-1117, 2006. A Daedal Positioning Systems model 2525 rotatory positioning stage (Parker Hannifin Corp, Daedal Division, Irwin, Pa.) with a custom attachment was used to measure the angle of needle insertion to the horizontal. Two ultrasonic imaging processes were used in this experiment: traditional B-mode and ARFI imaging. Two types of acoustic beams are used to generate ARFI displacement images: high-intensity pushing beams and conventional B-mode tracking beams. See M. Palmeri, S. McAleavey, G. Trahey, and K. Nightingale, "Ultrasonic tracking of acoustic radiation force-induced displacements in homogeneous media," *IEEE Trans Ultras Ferroelec Freq Control*, vol. 53, no. 7, pp. 1300-1313, 2006; M. Palmeri, *Imaging the mechanical properties of tissue with ultrasound: An investigation of the response of soft tissue to acoustic radiation force*. PhD thesis, Duke University, 2005; K. Nightingale, M. Soo, M. Palmeri, A. Congdon, K. Frinkley, and G. Trahey, "Imaging tissue mechanical properties using impulsive acoustic radiation force," in *IEEE Biomedical Imaging Symposium*, no. 1, pp. 41-44, 2004. The beams were created by a Siemens VF7-3 linear array (5.33 MHz center frequency), and were electronically laterally focused at 25 mm, with an F/2 focal configuration, and had a fixed elevation focus near 37.5 mm unless otherwise specified. To generate an ARFI image, a reference tracking beam is fired, followed by a pushing beam. The pushing beams are similar to color Doppler pulses, but with unapodized apertures and longer pulse lengths (400 cycles) for a duration of 95 µs. The pushing beam was followed by a series of 50 tracking beams at 5.33 MHz in typical A-line configuration fired at a pulse repetition frequency (PRF) of 7 kHz for an overall tracking duration of up to 7 ms in each pushing location. The lateral field of view was 25 mm, obtained with 36 pushing locations and four parallel receive tracking beams with uniform lateral spacing. J. Dahl, M. Palmeri, V. Agrawal, K. Nightingale, and G. Trahey, "A parallel tracking method for acoustic radiation force impulse imaging," *IEEE Trans Ultras Ferroelec Freq Control*, vol. 54, no. 2, pp. 301-312, 2007. The transducer was held with a motorized translation stage (model NM 3000, 0.1 µm precision, Newport Corporation, Irvine, Calif.). The custom pulse sequence was fired, and IQ data were stored for off-line processing. An additional B-mode image was stored as well for comparison with the ARFI data and registration. Local displacement estimates were acquired using the Loupas phase-shift estimator and 1-D cross correlation between sequentially acquired tracking lines. The complete ARFI dataset yields displacement estimates through time for a 2-D region of interest. See T. Loupas, R. Peterson, and R. Gill, "Experimental evaluation of velocity and power estimation for ultrasound blood flow imaging, by means of a two-dimensional autocorrelation approach," *IEEE Trans Ultras Ferroelec Freq Control*, vol. 42, pp. 689-699, 1995. G. Pinton, J, Dahl, and G. Trahey, "Rapid tracking of small displacements with ultrasound," *IEEE Trans Ultrason Ferroelec Freq Control*, vol. 53, no. 6, pp. 1103-1117, 2006. G. Trahey, J. Allison, and O. VonRamm, "Angle independent ultrasonic detection of blood flow," *IEEE BME*, vol. BME-34, no. 12, pp. 965-967, 1987. M. Palmeri, S. McAleavey, G. Trahey, and K. Nightingale, "Ultrasonic tracking of acoustic radiation force-induced displacements in homogeneous media," *IEEE Trans Ultras Ferroelec Freq Control*, vol. 53, no. 7, pp. 1300-1313, 2006.

Needle Visualization Overlay Implementation

The needle visualization overlay techniques according to some embodiments of the invention were applied to datasets obtained using horizontal 18, 21, and 25 gauge needles at 16 locations on and elevationally off-axis to the transducer in 0.25 mm increments, and to 18 G needles on the transducer axis between 5 and 30 degrees to the horizontal, as shown in FIGS. 6A-6B. The visualized needle obtained through the overlay techniques described herein was compared to the original ARFI images, the B-mode images, and cross-sectional examination of the graphite phantoms. R. Gonzalez and R. Woods, *Digital Image Processing*. New Jersey: Prentice-Hall, 2001. While many existing ultrasound segmentation techniques require user input, the needle visualization technique presented here is a fully automated approach based on underlying features of the ARFI image. The contrast threshold was based on the assumption a near Gaussian distribution of pixel values inside and outside the needle to generate a fixed global contrast threshold over all three needle gauges. In order to ensure automaticity, the contrast threshold was not adjusted in the remaining testing. The preset contrast, correlation coefficient cutoff, and smoothing functions generally do not require real-time user input.

Registration with B-mode

Image registration is the construction of a composite medical image from overlapping images. M. Thomas, M. Joachim, V. Hans, and G. Maggie, "Medical image processing toolbox in matlab: Registration, masters thesis," *University College of Antwerpen, Belgium*, 2006. Often, this process involves a linear transformation between two images, though it can frequently require other processing if there is skewing of the images. Image matching has previously been accomplished between ARFI and B-mode images acquired using the same transducer. K. Nightingale, M. Palmeri, and G. Trahey, "Analysis of contrast in images generated with transient acoustic radiation force," *Ultrasound Med. Biol.*, vol. 32, no. 1, pp. 61-72, 2006. For the needle and B-mode images, the registration process was a linear scaling transformation between the binary needle image mask created from the ARFI data and the B-mode image. The consistent beam locations between the two image acquisitions mean that the datasets are inherently coregistered, an advantage intrinsic to acquiring the B-mode and ARFI datasets with the same transducer. The needle prediction output of the segmentation techniques were turned into a mask for the existing B-mode image without needing modifications. Depending on clinician preference, the mask can be opaque or transparent, and can allow the clinician to view the needle relative to familiar B-mode landmarks. The needle was displayed in the registered image as having the radius equal to the axial standard deviation of the needle prediction points. This radius was used for research purposes as another way to identify how many points were being kept in the continuity constraint, and the focus of the clinical interest and evaluation of the techniques lies in identification of the needle tip. B. Sites, J. Neal, and V. Chan, "Ultrasound in regional anesthesia: Where should the "focus" be set?," *Regional Anesthesia and Pain Medicine*, vol. 34, no. 6, pp. 531-533, 2009.

Needle Tip Localization—Gold Standard Identification

Visualization of the needle tip is particularly important for clinical applications to identify where surrounding anatomical structures are located in comparison to the needle. In order to perform a quantitative evaluation of the accuracy of the ARFI-based needle segmentation, the needle tip location had to be verified. The 200 bloom graphite phantoms were cut open along the needle plane and the location of the needle tip was measured as shown in FIGS. 15A-15B.

Results

Comparison to B-mode

Figure 17A:
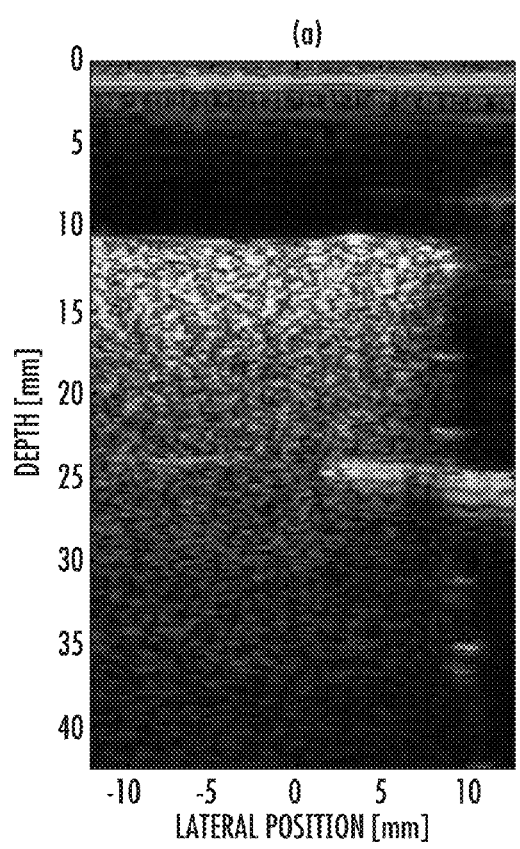
FIG. 17A-17B are digital images of a horizontal 25 G needle in a 200 bloom graphite phantom on-axis in elevation to the transducer.
Figure 17B:
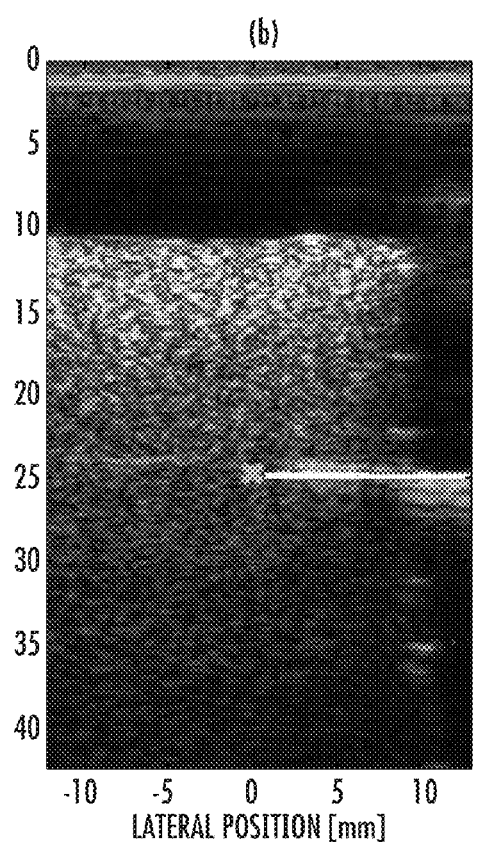
Figures 18A, 18B, 18C, 18D, 18E, 18F:
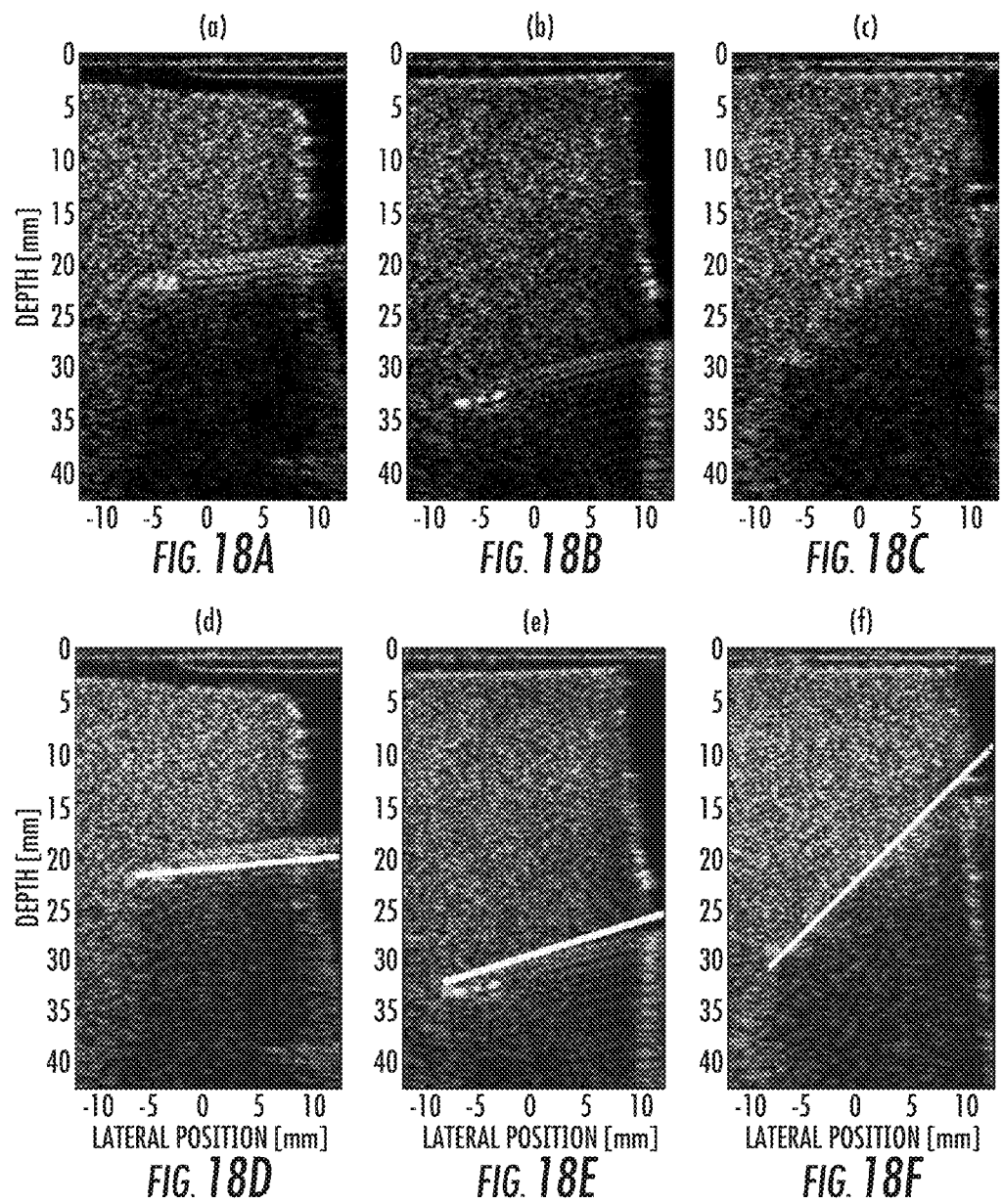
FIGS. 18A-18F are B-mode images of an angled 18 G needle in a 200 bloom graphite phantom at different angles with respect to the horizontal without (FIGS. 18A-18C) and with (FIGS. 18D-18F) needle visualization overlay applied.
Figure 20A:
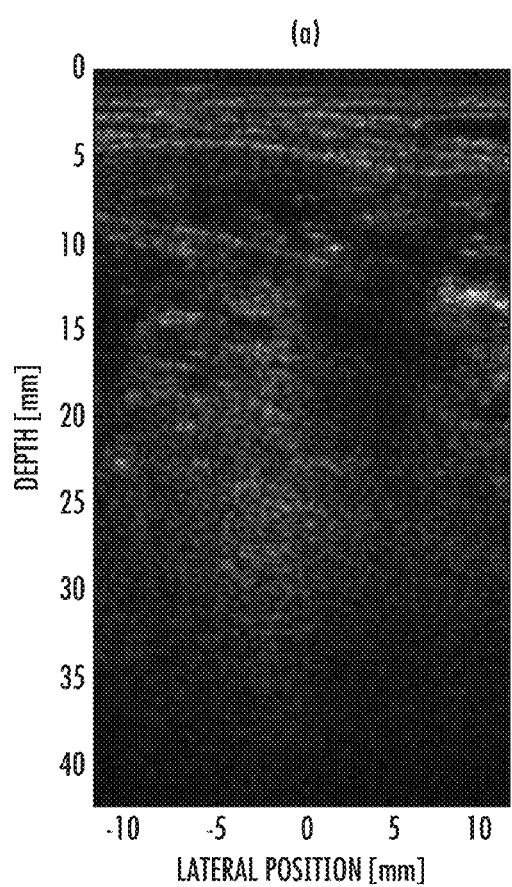
FIG. 20A-20B are digital images of the an in vivo intrascalene injection after 2 cc injection of saline.
Figure 20B:
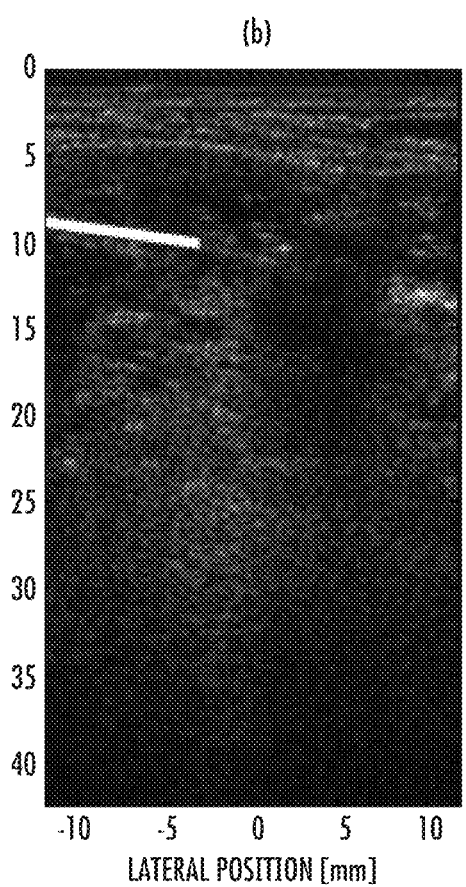

Example overlaid binary needle images with co-registered B-mode images are shown in FIGS. 16A-16F for various elevation offsets between the horizontal needle and transducer imaging plane. FIGS. 17A-17B provide an example with a smaller (25 G) needle. The needle visualization overlay was also applied to needles at angles on-axis (FIGS. 18A-18F), on horizontal needles in degassed lean bovine muscle (FIGS. 19A-19F), and in a live subject (FIG. 20A-20B).

Quantitative Metrics

Figure 22B:
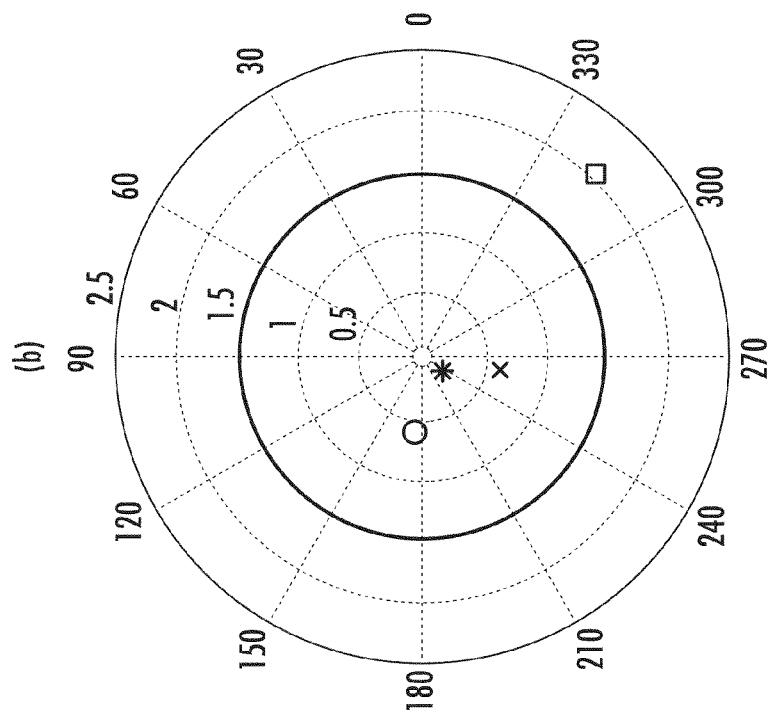
FIG. 22B is a graph of the distribution of actual needle tip location versus needle tip prediction across all angles of needle insertion with the actual needle tip location at the center of the plot. The inner circle represents a 1.5 mm radius around the actual needle tip position. Images were acquired of 18 G needles in a 200 bloom graphite phantom at several angles to the horizontal with alignment between the long axis of the needle and the transducer imaging plane.
Figure 22A:
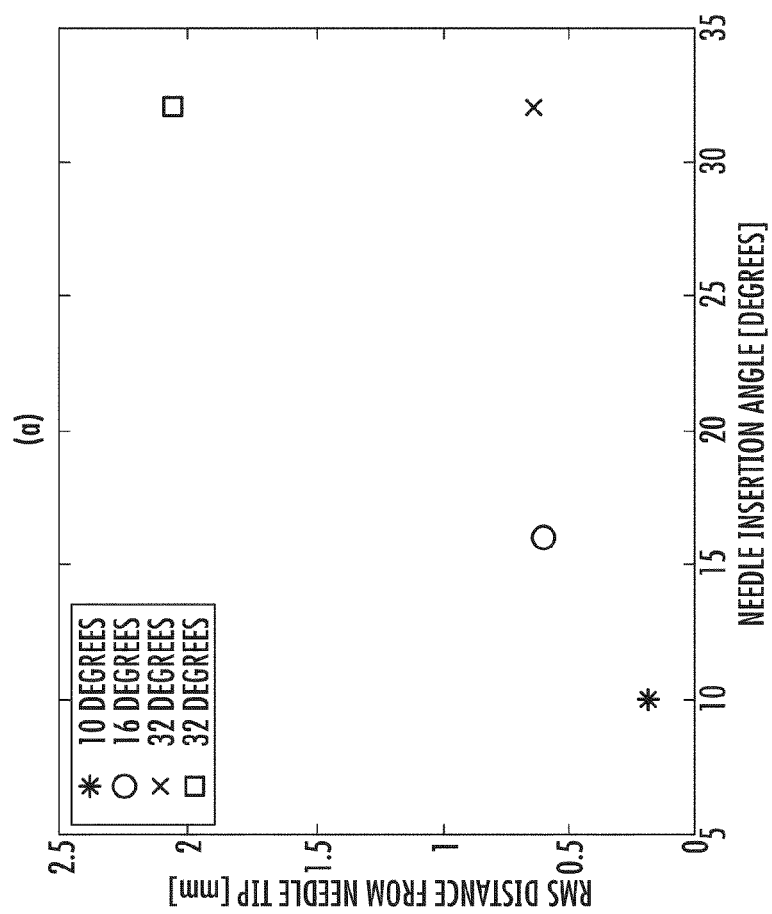
FIG. 22A is a graph of the RMS error of tip prediction versus needle insertion angle.

Needle Tip Visualization: Needle tip prediction accuracy is particularly important for clinical applications especially influencing success rate of intravenous catheterization and regional anesthesia and avoidance of damage to surrounding tissue structures. The difference between the needle tip prediction output and the actual needle tip location can be viewed in the form of a polar plot. FIG. 21B shows the root-mean-square (RMS) error and angular position of the needle prediction with respect to the center of the plot, the location of the actual needle tip in the axiallateral plane. The RMS distance between the tip prediction and actual tip location as a function of elevation offset from the transducer are shown in FIG. 21A. FIG. 22 shows the differences between needle tip prediction and needle tip location for the 18 G needles inserted at various angles.

Discussion

In the areas of regional anesthesia, central venous catheter placement, and tissue biopsy, B-mode ultrasound has been useful to aid needle guidance, increase success rate, and prevent injuries to surrounding tissues. J. French, N. Raine-Fenning, N. Hardman, and N. Bedforth, "Pitfalls of ultrasound guided vascular access: the use of three/four-dimensional ultrasound," *Anaesthesia*, vol. 63, pp. 806-813, 2008. M. Abrahams, M. Aziz, R. Fu, and J.-L. Horn, "Ultrasound guidance compared with electrical neurostimulation for peripheral nerve block: a systematic review and meta-analysis of randomized controlled trials," *British Journal of Anaesthesia*, vol. 103, no. 3, pp. 408-417, 2009. Currently, the clinician suffers from two primary difficulties with ultrasound needle guidance that are addressed by the techniques presented here: visualization of needles that have elevation offset from the transducer imaging plane, and visualization of needles at steep angles. In clinical settings, where a nerve or vessel has been visualized with B-mode but the needle cannot be seen, these techniques may be implemented for the clinician to determine the needle tip location. In the clinical settings of regional anesthesia, central venous catheter placement, and tissue biopsy, the needle tip should be visualized within the diameter of the object which the needle is targeting. Since the smallest vessels, nerves, and biopsy targets are 2 mm in diameter, an appropriate target for these techniques would for RMS error within 2 mm. K. Chin, A. Perlas, V. Chan, and R. Brull, "Needle visualization in ultrasound-guided regional anesthesia: Challenges and solutions," *Regional Anesthesia and Pain Medicine*, vol. 33, no. 6, pp. 532-544, 2008; P. Peng and S. Narouze, "Ultrasound-guided interventional procedures in pain medicine: A review of anatomy, sonoanatomy, and procedures," *Regional Anesthesia and Pain Medicine*, vol. 34, no. 5, 2009. The accuracy of needle tip prediction using suggests that implementation would be a clinically useful tool. As shown in FIGS. 21A-21B, the needle visualization overlay performs particularly well with elevation offsets up to 1.5 mm away, where the needle tip prediction is likely to be within 2 mm of the actual needle tip location. FIGS. 21A-21B demonstrate the effectiveness of predicting horizontal needle tip over three different gauges with the automated needle segmentation. The visualization techniques performed well for all three needle gauges, yielding tip estimates 2 mm or closer to the actual needle tip location in the axial-lateral plane within 1.5 mm of the needle axis. While the visualization overlay performed worse for the 25 G needle, the fact that this needle has the smallest outer diameter means that it is also the most difficult to see in traditional B-mode, so the improvement of the algorithm for visualization (as shown in FIGS. 17A 17B and 19A-19F)) over traditional B-mode is still impressive. An additional advantage is that estimates that are not near the needle may be eliminated because of the strict correlation coefficient cutoff. Thus, while datasets were acquired up to 4 mm elevationally off-axis to the needle in all 3 needle gauges, the techniques only yielded needle predictions within 1 mm of the needle for the 21 G and 25 G needles and out to 1.75 mm for the 18 G needle. This automaticity ensures that the needle estimates are likely to be near the actual needle tip location, rather than identifying lines in an image that do not correspond to needle location. Needles at angles to the horizontal present challenges to the physician in traditional B-mode visualization, but were all well-visualized with the needle segmentation as shown in FIGS. 18A-18F. While one of the 32-degree angle example predictions had an RMS error greater than 2 mm, this level of detail still gives important information to the clinician about general needle location. As one can see in FIGS. 19C and 19F, angled needles can be extremely difficult to see in B-mode images. Thus, identification of the needle tip to within 2 mm of its actual location is a dramatic improvement over existing methods and within the diameter of the object targeted by the needle in current applications. While the needle tip prediction is close to the actual needle tip location in the axial/lateral plane, the elevation offset from the transducer imaging plane in which the prediction outputs a needle estimate could impose a needle tip interpretation error. For the applications to regional anesthesia and central venous access, however, the important information for the clinician is the location of the needle tip relative to other structures in the B-mode. Having a needle tip identification technique that can tell the clinician that the needle is close to a desired anatomic detail of interest (such as a nerve or vessel) will allow the clinician to easily shift the transducer to an on-axis view in which a nerve and needle can be visualized together in the B-mode image. The live-imaging and bovine muscle examples shown in FIGS. 19A-19F and 20A-20B provide further evidence of future clinical utility of some embodiments according to the invention. Since many nerves are anatomically located near muscle, the needle can often be confused with the horizontal striations in B-mode, a confusion that is particularly obvious in FIGS. 19B and 19C. FIGS. 20A-20B demonstrate the utility of the needle segmentation and visualization techniques in a clinical setting of an intrascalene injection of a subject's brachial plexus. While it appears that the actual needle extends beyond the segmented section, this is likely due to the fact that this image was acquired after 2 cc of saline were injected, leading to decorrelation near the needle tip which was probably removed during the decorrelation-removal step. There are also several striations close to the surface which might be confused for the needle, but the needle path was correctly identified and may in the future correctly identify the needle tip if datasets are acquired prior to injection of saline.

Conclusions

Information gleaned from ARFI images of needles in tissue can supplement traditional B-mode to provide clinically useful needle visualization. The ease of registration to B-mode images, the robust nature of the needle identification techniques, and the lack of required user input are well-suited to translation to the clinical setting. Improvements in patient care can be achieved by identification of needle position, particularly in the areas of regional anesthesia, tissue biopsy, and central venous access. As discussed herein, the needle visualization algorithm can successfully identify needle tips to within 2 mm of their actual position up to 1.5 mm off-axis from the imaging plane.

In addition, the needle visualization algorithm worked well for needle angles between 0 and 35 degrees, with particular improvement over B-mode visualization in the more angled cases. Some embodiments according to the invention using a modified smoothing function may also be useful in identification of other implanted medical hardware, such as cardiac devices and brachytherapy seeds.

Information gleaned from ARFI images of needles in tissue according to embodiments of the present invention can supplement traditional B-mode to provide clinically useful needle visualization. The ease of registration to B-mode images, the robust nature of the needle identification calculation, and the lack of required user input make this calculation well-suited to translation to the clinical setting. Improvements in patient care can be achieved by identification of needle position, particularly in the areas of regional anesthesia and central venous access. The needle visualization calculation is successful at identification of the needle tip to within 1.5 mm between 1 mm off-axis from the transducer imaging plane and 2.5 mm off-axis from the transducer imaging plane. In addition, the needle visualization calculation worked well for needle angles between 0 and 30 degrees, with particular improvement over B-mode visualization in the steeper angled cases.

Although embodiments according to the present invention are described herein with respect to needle visualization, the exemplary calculations can be used, for example, with a modified smoothing function, in identification of other implanted medical hardware such as cardiac devices and brachytherapy seeds. Moreover, other types of imaging data can be used, including three-dimensional ultrasound images and/or elasticity-based images (such as Magnetic Resonance Elastography or Strain Elastography). Although some embodiments are described herein with respect to ARFI images that are used to detect object or needle positions, other techniques to detect regions of increased stiffness, perceived stiffness or any imaging modality in which the needle placement may be detected with suitable contrast with the surrounding tissue may be used.

The present invention may be embodied as methods, electronic devices, and/or computer program products. Some embodiments of the present invention were described above with reference to block diagrams and/or operational illustrations of methods and electronic devices. In this regard, each block may represent a module, segment, or portion of code, which comprises one or more executable instructions for implementing the specified logical function(s). It is to be understood that each block of the block diagrams and/or operational illustrations, and combinations of blocks in the block diagrams and/or operational illustrations can be embodied on analog circuitry and/or digital circuitry. These program instructions may be provided to a controller circuit, which may include one or more general purpose processors, special purpose processors, ASICs, and/or other programmable data processing apparatus, such that the instructions, which execute via the controller, create means for implementing the functions/acts specified in the block diagrams and/or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

These computer program instructions may also be stored in a computer-usable or computer-readable memory that may direct a controller circuit to function in a particular manner, such that the instructions stored in the computer usable or computer-readable memory produce an article of manufacture including instructions that implement the function specified in the flowchart and/or block diagram block or blocks. The computer-usable or computer-readable medium may be, for example but not limited to, an electronic, magnetic, optical, electromagnetic, or semiconductor system, apparatus, or device. More specific examples (a nonexhaustive list) of the computer-readable medium include the following: hard disk devices, optical storage devices, magnetic storage devices, random access memory (RAM) devices, read-only memory (ROM) devices, erasable programmable read-only memory (EPROM or Flash memory) devices, and compact disc read-only memory (CD-ROM).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An imaging system for identifying a presence of an object in a tissue region of interest, the system comprising:
   a controller configured to obtain first and second image data sets from the region of interest;
   a contrast identification module configured to identify a contrasting region of altered stiffness in the first image data set corresponding to an object in the tissue region of interest; and
   an image data enhancement module configured to identify the object in the second image data set based on the contrasting region of altered stiffness in the first image data set.

2. The system of claim 1, wherein the first image data set is an Acoustic Radiation Force Impulse (ARFI) image data set that is obtained concurrently with the second image data set.

3. The system of claim 2, wherein the second image data set is a B-mode ultrasound image data set.

4. The system of claim 3, wherein the image data enhancement module is further configured to enhance a contrast level of the region of altered stiffness corresponding to the object.

5. The system of claim 3, wherein the image data enhancement module is configured to determine a third image data set that comprises the B-mode image data set and the region of altered stiffness from the ARFI image data set.

6. The system of claim 5, wherein the object comprises a medical device.

7. The system of claim 6, wherein the image data enhancement module is configured to identify the object based on predetermined characteristics of the object.

8. The system of claim 7, wherein the object comprises an elongated needle, and the image enhancement module is configured to conform the region of increased stiffness to generally correspond to an elongated shape corresponding to the needle.

9. The system of claim 6, wherein the object comprises an elongated needle having a tip portion in the region of interest, and the image data enhancement module is configured to identify the tip portion of the needle.

10. The system of claim 1, wherein the first and second image data sets are concurrently obtained from a common ultrasound transducer or transducer array.

11. A method for identifying a presence of an object in a tissue region of interest, the method comprising:
   obtaining first and second image data sets from the region of interest;
   identifying a contrasting region of altered stiffness in the first image data set corresponding to an object in the tissue region of interest; and
   identifying the object in the second image data set based on the contrasting region of altered stiffness in the first image data set.

12. The method of claim 11, wherein the first image data set is an Acoustic Radiation Force Impulse (ARFI) image data set that is obtained concurrently with the second image data set.

13. The method of claim 12, wherein the second image data set is a B-mode ultrasound image data set.

14. The method of claim 13, further comprising enhancing a contrast level of the region of altered stiffness corresponding to the object.

15. The method of claim 13, further comprising determining a third image data set that comprises at least a portion of the first image data set and at least a portion of the second image data set.

16. The method of claim 15, wherein the object comprises a medical device.

17. The method of claim 16, wherein the image data enhancement module is configured to identify the object based on predetermined characteristics of the object.

18. The method of claim 17, wherein the object comprises an elongated needle, the method further comprising generally conforming the region of increased stiffness to generally correspond to an elongated shape corresponding to the needle.

19. The method of claim 17, wherein the object comprises an elongated needle having a tip portion, the method further comprising identifying the tip portion of the needle.

20. The method of claim 11, wherein the first and second image data sets are concurrently obtained from a common ultrasound transducer or transducer array.

* * * * *